(12) United States Patent
Langdale et al.

(10) Patent No.: US 11,612,422 B2
(45) Date of Patent: *Mar. 28, 2023

(54) STABILIZATION SYSTEMS

(71) Applicant: GLOBUS MEDICAL, INC., Audubon, PA (US)

(72) Inventors: Evan Langdale, Philadelphia, PA (US); Henry Rutledge, Lansdale, PA (US); James A. Gault, Philadelphia, PA (US); Andrew Davison, Downingtown, PA (US); Barclay Davis, Glenmoore, PA (US); Kevin Gahman, Douglassville, PA (US)

(73) Assignee: Globus Medical Inc., Audubon, PA (US)

( * ) Notice: Subject to any disclaimer, the term of this patent is extended or adjusted under 35 U.S.C. 154(b) by 343 days.

This patent is subject to a terminal disclaimer.

(21) Appl. No.: 16/858,785

(22) Filed: Apr. 27, 2020

(65) Prior Publication Data

US 2020/0253652 A1 Aug. 13, 2020

Related U.S. Application Data

(63) Continuation of application No. 15/238,772, filed on Aug. 17, 2016, now Pat. No. 10,687,873.

(51) Int. Cl.
*A61B 17/80* (2006.01)
*A61B 17/86* (2006.01)
(Continued)

(52) U.S. Cl.
CPC ...... *A61B 17/8042* (2013.01); *A61B 17/1728* (2013.01); *A61B 17/7059* (2013.01); *A61B 17/8014* (2013.01); *A61B 17/8052* (2013.01); *A61B 17/8057* (2013.01); *A61B 17/8061* (2013.01); *A61B 17/86* (2013.01); *A61B 17/8605* (2013.01); *A61B 17/808* (2013.01);
(Continued)

(58) Field of Classification Search
CPC . A61B 17/80; A61B 17/8042; A61B 17/8014; A61B 17/8052; A61B 17/8057; A61B 17/86; A61B 17/8605
See application file for complete search history.

(56) References Cited

U.S. PATENT DOCUMENTS

| 1,105,105 A | 7/1914 | Sherman |
| 2,486,303 A | 10/1949 | Longfellow |

(Continued)

FOREIGN PATENT DOCUMENTS

| DE | 102010025702 A1 | 1/2012 |
| JP | 1190348 A | 7/1989 |

(Continued)

*Primary Examiner* — Christopher J Beccia

(57) ABSTRACT

Devices, systems, and methods of bone stabilization. The bone stabilization system includes a bone plate having an upper surface and a lower surface configured to be in contact with bone, the bone plate having an opening extending from the upper surface to the lower surface. The opening is configured to receive a fastener, which may be either a locking fastener or a compression fastener. The locking fastener has a threaded head portion configured to engage and lock to the bone plate, and the compression fastener is configured to dynamically compress the bone.

16 Claims, 23 Drawing Sheets

(51) Int. Cl.
*A61B 17/17* (2006.01)
*A61B 17/70* (2006.01)
*A61B 17/00* (2006.01)

(52) U.S. Cl.
CPC ......... *A61B 17/809* (2013.01); *A61B 17/8047* (2013.01); *A61B 2017/00858* (2013.01)

(56) References Cited

U.S. PATENT DOCUMENTS

| | | | |
|---|---|---|---|
| 4,493,317 A | 1/1985 | Klaue | |
| 4,513,744 A | 4/1985 | Klaue | |
| 4,524,765 A | 6/1985 | de Zbikowski | |
| 4,651,724 A | 3/1987 | Berentey et al. | |
| 4,781,183 A | 11/1988 | Casey et al. | |
| 4,867,144 A | 9/1989 | Karas et al. | |
| 5,002,544 A | 3/1991 | Klaue et al. | |
| 5,041,114 A | 8/1991 | Chapman et al. | |
| 5,053,036 A | 10/1991 | Perren et al. | |
| 5,151,103 A | 9/1992 | Fepic et al. | |
| 5,259,398 A | 11/1993 | Vrespa | |
| 5,364,399 A | 11/1994 | Lowery et al. | |
| 5,372,598 A | 12/1994 | Luhr et al. | |
| 5,423,826 A | 6/1995 | Coates et al. | |
| 5,601,553 A | 2/1997 | Trebing et al. | |
| 5,676,667 A | 10/1997 | Hausman | |
| 5,702,396 A | 12/1997 | Hoenig et al. | |
| 5,709,686 A | 1/1998 | Talos et al. | |
| 5,718,704 A | 2/1998 | Medoff | |
| 5,746,742 A | 5/1998 | Runciman et al. | |
| 5,785,712 A | 7/1998 | Runciman et al. | |
| 5,921,986 A | 7/1999 | Bonutti | |
| 5,938,664 A | 8/1999 | Winquist et al. | |
| 6,001,099 A | 12/1999 | Huebner | |
| 6,096,040 A | 8/2000 | Enser | |
| 6,139,550 A * | 10/2000 | Michelson | A61B 17/80 606/295 |
| 6,152,927 A | 11/2000 | Farris et al. | |
| 6,206,881 B1 | 3/2001 | Frigg et al. | |
| 6,283,969 B1 | 9/2001 | Grusin et al. | |
| 6,309,393 B1 | 10/2001 | Tepic et al. | |
| 6,322,562 B1 | 11/2001 | Wolter | |
| 6,364,882 B1 | 4/2002 | Orbay | |
| 6,533,786 B1 | 3/2003 | Needham et al. | |
| 6,623,486 B1 | 9/2003 | Weaver et al. | |
| 6,669,700 B1 | 12/2003 | Farris et al. | |
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,866,665 B2 | 3/2005 | Orbay | |
| 6,955,677 B2 | 10/2005 | Dahners | |
| 6,974,461 B1 | 12/2005 | Wolter | |
| 7,001,387 B2 | 2/2006 | Farris et al. | |
| 7,063,701 B2 | 6/2006 | Michelson | |
| 7,128,744 B2 | 10/2006 | Weaver et al. | |
| 7,137,987 B2 | 11/2006 | Patterson et al. | |
| 7,153,309 B2 | 12/2006 | Huebner et al. | |
| 7,179,260 B2 | 2/2007 | Gerlach et al. | |
| 7,250,053 B2 | 7/2007 | Orbay | |
| 7,294,130 B2 | 11/2007 | Orbay | |
| 7,322,983 B2 | 1/2008 | Harris | |
| 7,341,589 B2 | 3/2008 | Weaver et al. | |
| 7,354,441 B2 | 4/2008 | Frigg | |
| 7,604,657 B2 | 10/2009 | Orbay et al. | |
| 7,635,381 B2 | 12/2009 | Orbay | |
| 7,637,928 B2 | 12/2009 | Fernandez | |
| 7,655,029 B2 | 2/2010 | Niederberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,776,076 B2 | 8/2010 | Grady, Jr. et al. | |
| 7,857,838 B2 | 12/2010 | Orbay | |
| 7,867,260 B2 | 1/2011 | Meyer et al. | |
| 7,867,261 B2 | 1/2011 | Sixto, Jr. et al. | |
| 7,875,062 B2 | 1/2011 | Lindemann et al. | |
| 7,905,910 B2 | 3/2011 | Gerlach et al. | |
| 7,909,858 B2 | 3/2011 | Gerlach et al. | |
| 7,951,178 B2 | 5/2011 | Jensen | |
| 7,951,179 B2 | 5/2011 | Matityahu | |
| 7,976,570 B2 | 7/2011 | Wagner et al. | |
| D643,121 S | 8/2011 | Millford et al. | |
| D646,785 S | 10/2011 | Milford | |
| 8,043,297 B2 | 10/2011 | Grady, Jr. et al. | |
| 8,057,520 B2 | 11/2011 | Ducharme et al. | |
| 8,062,296 B2 | 11/2011 | Orbay et al. | |
| 8,100,953 B2 | 1/2012 | White et al. | |
| 8,114,081 B2 | 2/2012 | Kohut et al. | |
| 8,118,846 B2 | 2/2012 | Leither et al. | |
| 8,167,918 B2 | 5/2012 | Strnad et al. | |
| 8,177,820 B2 | 5/2012 | Anapliotis et al. | |
| 8,246,661 B2 | 8/2012 | Beutter et al. | |
| 8,252,032 B2 | 8/2012 | White et al. | |
| 8,257,403 B2 | 9/2012 | Den Hartog et al. | |
| 8,257,405 B2 | 9/2012 | Haidukewych et al. | |
| 8,257,406 B2 | 9/2012 | Kay et al. | |
| 8,262,707 B2 | 9/2012 | Huebner et al. | |
| 8,317,842 B2 | 11/2012 | Graham et al. | |
| 8,323,321 B2 | 12/2012 | Gradl | |
| 8,337,535 B2 | 12/2012 | White et al. | |
| 8,343,155 B2 | 1/2013 | Fisher et al. | |
| 8,382,807 B2 | 2/2013 | Austin et al. | |
| 8,394,098 B2 | 3/2013 | Orbay et al. | |
| 8,394,130 B2 | 3/2013 | Orbay et al. | |
| 8,398,685 B2 | 3/2013 | McGarity et al. | |
| 8,403,966 B2 | 3/2013 | Ralph et al. | |
| 8,419,775 B2 | 4/2013 | Orbay et al. | |
| 8,444,679 B2 | 5/2013 | Ralph et al. | |
| 8,506,608 B2 | 8/2013 | Cerynik et al. | |
| 8,512,385 B2 | 8/2013 | White et al. | |
| 8,518,090 B2 | 8/2013 | Huebner et al. | |
| 8,523,862 B2 | 9/2013 | Murashko, Jr. | |
| 8,523,921 B2 | 9/2013 | Horan et al. | |
| 8,551,095 B2 | 10/2013 | Fritzinger et al. | |
| 8,568,462 B2 | 10/2013 | Sixto, Jr. et al. | |
| 8,574,268 B2 | 11/2013 | Chan et al. | |
| 8,597,334 B2 | 12/2013 | Mocanu | |
| 8,603,147 B2 | 12/2013 | Sixto, Jr. et al. | |
| 8,617,224 B2 | 12/2013 | Kozak et al. | |
| 8,632,574 B2 | 1/2014 | Kortenbach et al. | |
| 8,641,744 B2 | 2/2014 | Weaver et al. | |
| 8,728,126 B2 | 5/2014 | Steffen | |
| 8,740,905 B2 | 6/2014 | Price et al. | |
| 8,747,442 B2 | 6/2014 | Orbay et al. | |
| 8,764,808 B2 | 7/2014 | Gonzalez-Hernandez | |
| 8,777,998 B2 | 7/2014 | Daniels et al. | |
| 8,790,376 B2 | 7/2014 | Fritzinger et al. | |
| 8,808,333 B2 | 8/2014 | Kuster et al. | |
| 8,808,334 B2 | 8/2014 | Strnad et al. | |
| 8,834,537 B2 | 9/2014 | Castaneda et al. | |
| 8,852,246 B2 | 10/2014 | Hansson | |
| 8,852,249 B2 | 10/2014 | Ahrens et al. | |
| 8,864,802 B2 | 10/2014 | Schwager et al. | |
| 8,870,931 B2 | 10/2014 | Dahners et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |
| 8,926,675 B2 | 1/2015 | Leung et al. | |
| 8,940,026 B2 | 1/2015 | Hilse et al. | |
| 8,940,028 B2 | 1/2015 | Austin et al. | |
| 8,940,029 B2 | 1/2015 | Leung et al. | |
| 8,951,291 B2 | 2/2015 | Impellizzeri | |
| 8,968,368 B2 | 3/2015 | Tepic | |
| 9,011,457 B2 | 4/2015 | Grady, Jr. et al. | |
| 9,023,052 B2 | 5/2015 | Lietz et al. | |
| 9,050,151 B2 | 6/2015 | Schilter | |
| 9,072,555 B2 | 7/2015 | Michel | |
| 9,107,678 B2 | 8/2015 | Murner et al. | |
| 9,107,711 B2 | 8/2015 | Hainard | |
| 9,107,713 B2 | 8/2015 | Horan et al. | |
| 9,107,718 B2 | 8/2015 | Isch | |
| 9,113,970 B2 | 8/2015 | Lewis et al. | |
| 9,149,310 B2 | 10/2015 | Fritzinger et al. | |
| 9,161,791 B2 | 10/2015 | Frigg | |
| 9,161,795 B2 | 10/2015 | Chasbrummel et al. | |

(56) References Cited

U.S. PATENT DOCUMENTS

| | | | |
|---|---|---|---|
| 9,168,075 B2 | 10/2015 | Dell'Oca | |
| 9,179,950 B2 | 11/2015 | Zajac et al. | |
| 9,179,956 B2 | 11/2015 | Cerynik et al. | |
| 9,180,020 B2 | 11/2015 | Gause et al. | |
| 9,211,151 B2 | 12/2015 | Weaver et al. | |
| 9,259,217 B2 | 2/2016 | Fritzinger et al. | |
| 9,259,255 B2 | 2/2016 | Lewis et al. | |
| 9,271,769 B2 | 3/2016 | Batsch et al. | |
| 9,283,010 B2 | 3/2016 | Medoff et al. | |
| 9,314,284 B2 | 4/2016 | Chan et al. | |
| 9,320,554 B2 | 4/2016 | Greenberg et al. | |
| 9,322,562 B2 | 4/2016 | Takayama | |
| 9,433,407 B2 | 9/2016 | Fritzinger et al. | |
| 9,433,452 B2 | 9/2016 | Weiner et al. | |
| 9,468,479 B2 | 10/2016 | Marotta et al. | |
| 9,480,512 B2 | 11/2016 | Orbay | |
| 9,545,277 B2 | 1/2017 | Wolf et al. | |
| 10,687,873 B2 * | 6/2020 | Langdale | A61B 17/8052 |
| 2002/0045901 A1 | 4/2002 | Wagner et al. | |
| 2004/0097937 A1 | 5/2004 | Pike et al. | |
| 2005/0107796 A1 | 5/2005 | Gerlach et al. | |
| 2005/0131413 A1 | 6/2005 | O'Driscoll et al. | |
| 2005/0187551 A1 | 8/2005 | Orbay et al. | |
| 2005/0187553 A1 | 8/2005 | Grabowski et al. | |
| 2005/0261688 A1 * | 11/2005 | Grady | A61B 17/8014 606/280 |
| 2006/0149265 A1 | 7/2006 | James et al. | |
| 2006/0195104 A1 * | 8/2006 | Schlafli | A61B 17/60 606/291 |
| 2006/0241607 A1 | 10/2006 | Myerson et al. | |
| 2007/0043366 A1 | 2/2007 | Pfefferle et al. | |
| 2007/0270849 A1 | 11/2007 | Orbay et al. | |
| 2008/0021477 A1 | 1/2008 | Strnad et al. | |
| 2008/0234677 A1 * | 9/2008 | Dahners | A61B 17/888 606/60 |
| 2008/0234749 A1 | 9/2008 | Forstein | |
| 2008/0275510 A1 | 11/2008 | Schonhardt et al. | |
| 2009/0024172 A1 | 1/2009 | Pizzicara | |
| 2009/0024173 A1 | 1/2009 | Reis, Jr. | |
| 2009/0118773 A1 | 5/2009 | James et al. | |
| 2009/0198285 A1 | 8/2009 | Raven, III | |
| 2009/0228010 A1 | 9/2009 | Gonzalez-Hernandez et al. | |
| 2009/0248084 A1 | 10/2009 | Hintermann | |
| 2009/0281543 A1 | 11/2009 | Orbay et al. | |
| 2009/0312760 A1 | 12/2009 | Forstein et al. | |
| 2010/0057086 A1 | 3/2010 | Price et al. | |
| 2010/0274247 A1 | 10/2010 | Grady, Jr. et al. | |
| 2011/0218580 A1 | 9/2011 | Schwager et al. | |
| 2012/0123484 A1 | 5/2012 | Lietz et al. | |
| 2012/0136396 A1 | 5/2012 | Baker et al. | |
| 2012/0265255 A1 | 10/2012 | Hilse et al. | |
| 2012/0323284 A1 | 12/2012 | Baker et al. | |
| 2013/0018426 A1 | 1/2013 | Tsai et al. | |
| 2013/0060291 A1 | 3/2013 | Petersheim | |
| 2013/0096630 A1 | 4/2013 | Lee et al. | |
| 2013/0123841 A1 | 5/2013 | Lyon | |
| 2013/0138156 A1 | 5/2013 | Derouet | |
| 2013/0150902 A1 | 6/2013 | Leite | |
| 2013/0165981 A1 | 6/2013 | Clasbrummet et al. | |
| 2013/0211463 A1 | 8/2013 | Mizuno et al. | |
| 2014/0005728 A1 | 1/2014 | Koay et al. | |
| 2014/0018862 A1 | 1/2014 | Koay et al. | |
| 2014/0031879 A1 | 1/2014 | Sixto, Jr. et al. | |
| 2014/0094856 A1 | 4/2014 | Sinha | |
| 2014/0121710 A1 | 5/2014 | Weaver et al. | |
| 2014/0180345 A1 | 6/2014 | Chan et al. | |
| 2014/0277178 A1 | 9/2014 | O'Kane et al. | |
| 2014/0277181 A1 | 9/2014 | Garlock | |
| 2014/0316473 A1 | 10/2014 | Pfeffer | |
| 2014/0330320 A1 | 11/2014 | Wolter | |
| 2014/0378975 A1 | 12/2014 | Castaneda et al. | |
| 2015/0051650 A1 | 2/2015 | Verstreken et al. | |
| 2015/0051651 A1 | 2/2015 | Terrill et al. | |
| 2015/0073486 A1 | 3/2015 | Marotta et al. | |
| 2015/0105829 A1 | 4/2015 | Laird | |
| 2015/0112355 A1 | 4/2015 | Dahners et al. | |
| 2015/0134011 A1 | 5/2015 | Medoff | |
| 2015/0142065 A1 | 5/2015 | Schonhardt et al. | |
| 2015/0190185 A1 | 7/2015 | Koay et al. | |
| 2015/0209091 A1 | 7/2015 | Sixto, Jr. et al. | |
| 2015/0216571 A1 * | 8/2015 | Impellizzeri | A61B 17/8057 264/279 |
| 2015/0223852 A1 | 8/2015 | Lietz et al. | |
| 2015/0272638 A1 | 10/2015 | Langford | |
| 2015/0282851 A1 | 10/2015 | Michel | |
| 2015/0313653 A1 | 11/2015 | Ponce et al. | |
| 2015/0313654 A1 | 11/2015 | Horan et al. | |
| 2015/0327898 A1 | 11/2015 | Martin | |
| 2015/0351816 A1 | 12/2015 | Lewis et al. | |
| 2016/0022336 A1 | 1/2016 | Bateman | |
| 2016/0030035 A1 | 2/2016 | Zajac et al. | |
| 2016/0045237 A1 | 2/2016 | Cerynik et al. | |
| 2016/0074081 A1 | 3/2016 | Weaver et al. | |
| 2016/0166297 A1 | 6/2016 | Mighell et al. | |
| 2016/0166298 A1 | 6/2016 | Mighell et al. | |
| 2016/0262814 A1 | 9/2016 | Wainscott | |
| 2016/0278828 A1 | 9/2016 | Ragghianti | |
| 2016/0310183 A1 | 10/2016 | Shaw et al. | |
| 2017/0042596 A9 | 2/2017 | Mighell et al. | |

FOREIGN PATENT DOCUMENTS

| | | |
|---|---|---|
| JP | H01190348 A | 7/1989 |
| JP | 2004529710 A | 9/2004 |
| JP | 2007151674 A | 6/2007 |
| JP | 2007289698 A | 11/2007 |
| JP | 2008-500143 A | 1/2008 |
| JP | 2008500143 A | 1/2008 |
| JP | 2008-505700 A | 2/2008 |
| JP | 2010-522019 A | 7/2010 |
| JP | 2013-521046 A | 6/2013 |
| JP | 2016530001 A | 9/2016 |
| WO | 2011109127 A1 | 9/2011 |
| WO | 2016134775 A1 | 9/2016 |

* cited by examiner

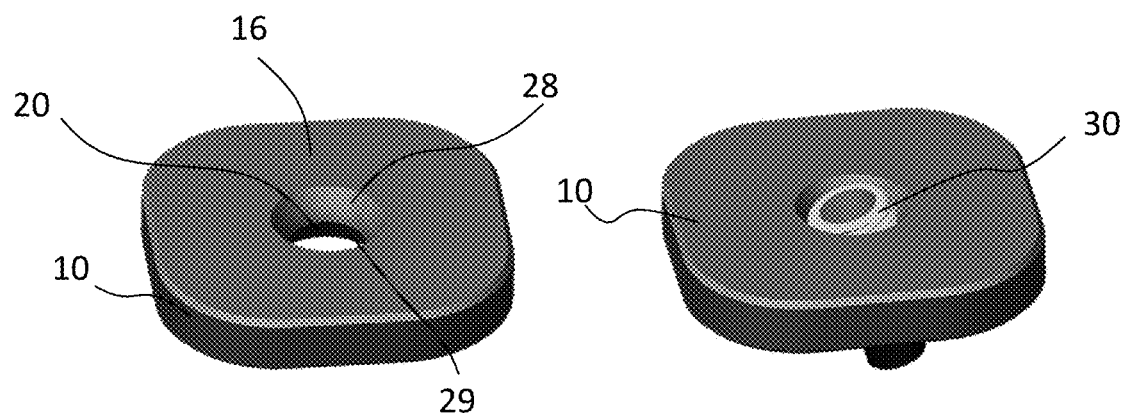
FIG. 26A
FIG. 26B
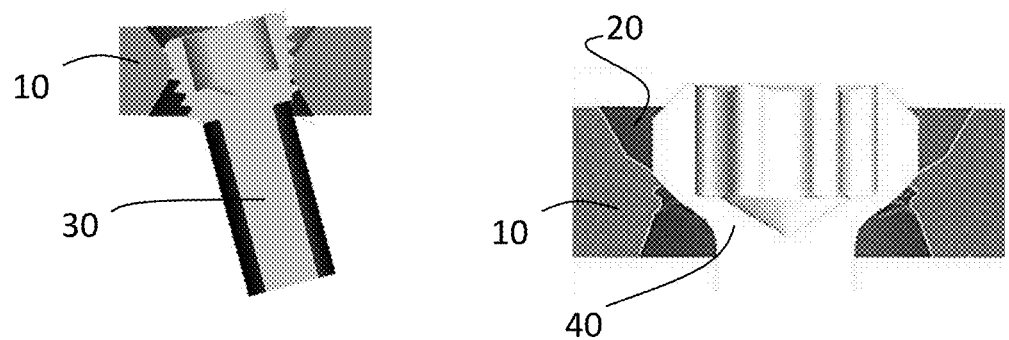
FIG. 26C
FIG. 26D

STABILIZATION SYSTEMS

CROSS REFERENCE TO RELATED APPLICATIONS

The present application is a continuation of U.S. patent application Ser. No. 15/238,772 filed on Aug. 17, 2016 which is incorporated in its entirety herein.

FIELD

The present disclosure relates to surgical devices, and more particularly, stabilization systems, for example, for trauma applications.

BACKGROUND

Bone fractures are often repaired by internal fixation of the bone, such as diaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture. Thus, there is a need for plating systems that provide stabilization to the appropriate anatomical area while providing appropriate locking and/or unlocking capability for dynamic compression of the bone.

SUMMARY

To meet this and other needs, devices, systems, and methods of bone stabilization are provided. The stabilization systems may include one or more plates and one or more fasteners. The fasteners may include locking and/or non-locking bone screws that a surgeon may select based on preference for a specific anatomical case. The locking fasteners may connect to the plate and the bone to thereby lock the plate to the bone. The non-locking fasteners may be able to dynamically compress the bone and create interfragmental compression.

According to one embodiment, a stabilization system includes a bone plate and a fastener. The bone plate has an upper surface and a lower surface configured to be in contact with bone, the bone plate having an opening extending from the upper surface to the lower surface. The opening includes a textured portion and non-textured portion, wherein the textured portion comprises a texture that is a non-threaded surface. The fastener is configured to be received by the opening and configured to be inserted into the bone. The opening is configured to receive either a locking fastener or a compression fastener. The locking fastener may have a threaded head portion configured to engage the textured portion and lock to the bone plate, and the compression fastener may have a substantially smooth head portion configured to dynamically compress the bone. The opening may include a combination compression and locking through hole formed by a first bore having a first bore axis and a second bore having a second bore axis different from the first bore axis. In some instances, one of the first and second bores may have an elongated opening, for example, to allow for translation of the non-locking, compression fastener.

According to another embodiment, a stabilization system includes a bone plate, a locking fastener, and a compression fastener. The bone plate has an upper surface and a lower surface configured to be in contact with bone, the bone plate having an opening extending from the upper surface to the lower surface, the opening including a textured portion and non-textured portion, wherein the textured portion comprises a texture that is a non-threaded surface. The locking fastener is configured to be received by one of the openings and configured to be inserted into the bone, wherein the locking fastener has a threaded head portion configured to lock to the bone plate. The compression fastener is configured to be received by one of the openings and configured to be inserted into the bone, wherein the compression fastener has a substantially smooth head portion configured to dynamically compress the bone. Each opening is configured to receive either the locking fastener or the compression fastener.

According to yet another embodiment, a stabilization system includes a bone plate and a fastener. The bone plate has an upper surface and a lower surface configured to be in contact with bone, the bone plate having an opening extending from the upper surface to the lower surface, wherein the opening is formed by at least three different partially overlapping bores including a first bore having at least a partial first internal thread, a second bore having at least a partial second internal thread, and a third bore having at least a partial third internal thread. The fastener is configured to be received by the opening and configured to be inserted into the bone, wherein the opening is configured to receive either a locking fastener or a compression fastener, the locking fastener having a threaded head portion configured to lock to the bone plate, and the compression fastener having a substantially smooth head portion configured to dynamically compress the bone.

Also provided are methods for installing the stabilization systems and kits including bone plates, fasteners, and components for installing the same.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 26A-26D depict a plate assembly according to one embodiment where a locking or non-locking fastener may be positioned at an angle or perpendicular to the plate.

DETAILED DESCRIPTION

Figure 1:
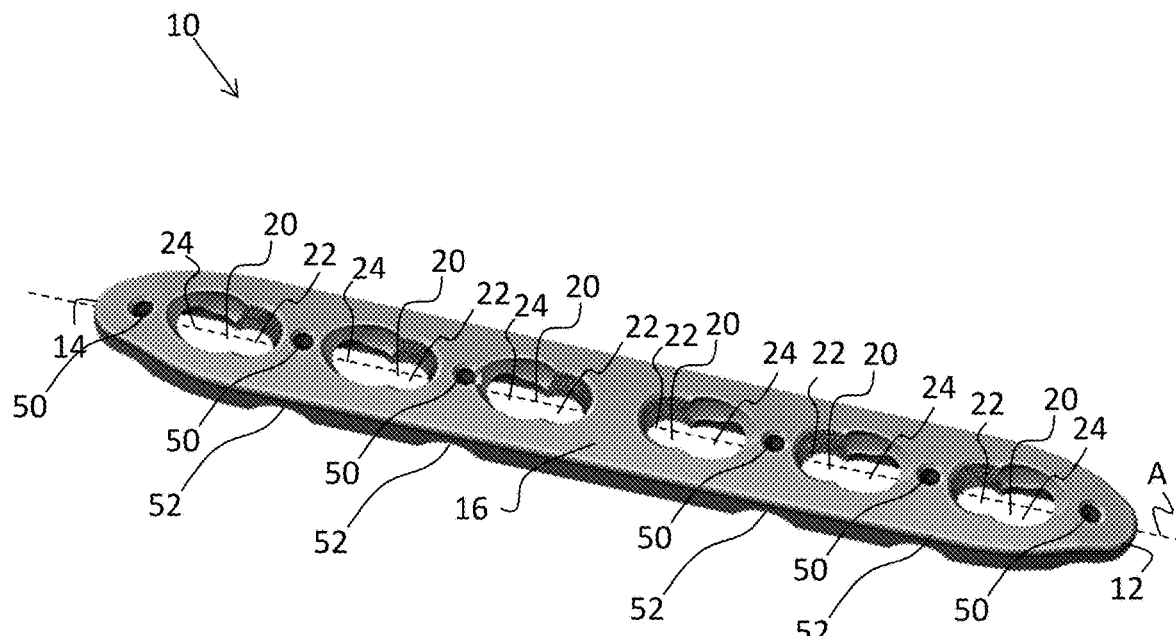
FIG. 1 depicts a top perspective view of a diaphyseal bone plate according to one embodiment.

Embodiments of the disclosure are generally directed to devices, systems, and methods for bone stabilization. Specifically, embodiments are directed to bone plating with locking and/or non-locking fasteners for dynamic compression of the bone. The hole designs may allow for fixed angle and/or polyaxial locking and/or non-locking of the fasteners. Some embodiments include blocking fasteners to prevent the bone fastener from backing out. Some embodiments further include locking fasteners with self-forming threads configured to displace the plate material, thereby locking the fastener to the plate.

The plates may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated.

The bone plate may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Referring now to the drawing, FIGS. 1-9 depict one embodiment of a plate 10 including one or more openings 20. The openings 20 extending through the plate 10 are configured to accept locking fasteners 30, non-locking fasteners 40, or a combination of both locking and non-locking fasteners 30, 40 that are able to dynamically compress the bone and/or affix the plate 10 to the bone. When plating diaphyseal bone, surgeons may use a combination of both locking and non-locking fasteners 30, 40 that are able to dynamically compress bone and to connect the bone and the plate 10. Dynamic compression may also be desirable to create interfragmental compression while tightening the fasteners 30, 40.

Figure 2:
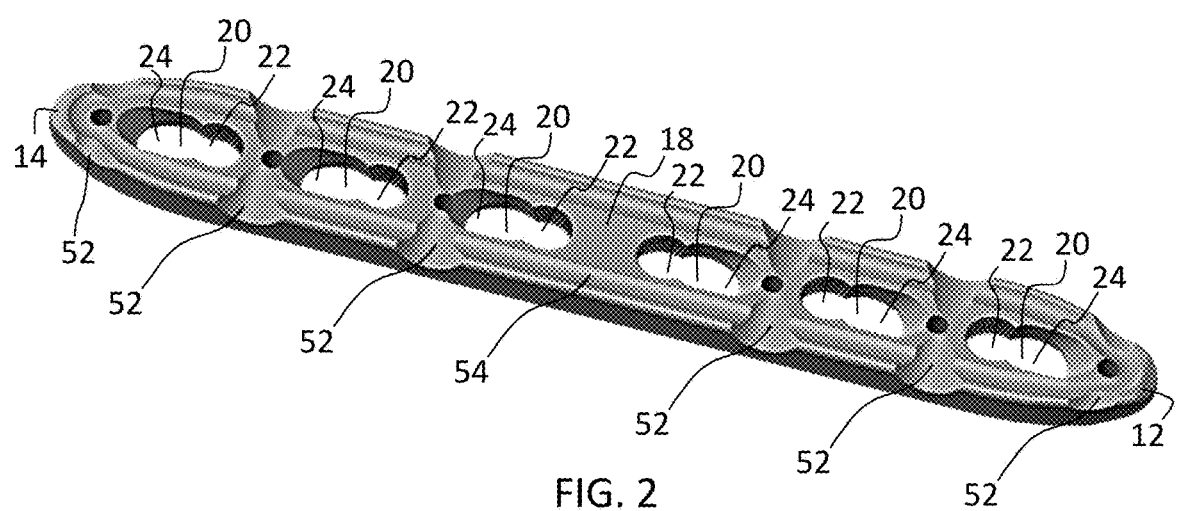
FIG. 2 depicts a bottom perspective view of the plate of FIG. 1.
Figure 3:
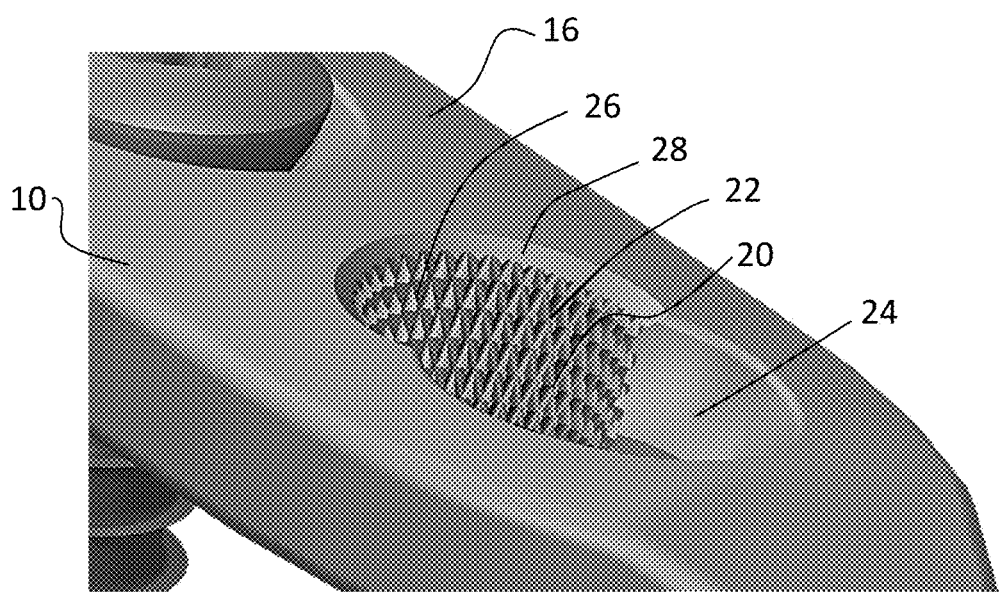
FIG. 3 is a close-up view of a combination hole according to one embodiment.

As shown in FIGS. 1 and 2, the plate 10 has a body that extends from a first end 12 to a second end 14 along a central longitudinal axis A. The plate 10 includes a top surface 16 and an opposite, bottom surface 18 configured to contact adjacent bone. The top and bottom surfaces 16, 18 are connected by opposite side surfaces extending from the first to second ends 12, 14 of the plate 10. Although the plate 10 is shown having a generally longitudinal body, it will be appreciated that any suitable shape and contouring of the plate 10 may be provided depending on the location and type of fracture to be plated.

The plate 10 includes one or more through openings 20 configured to receive one or more bone fasteners 30, 40. The openings 20 extend through the body of the plate 10 from the top surface 16 to the bottom surface 18. Each of the openings 20 may be in the form of a combination opening that has at least two overlapping holes. As shown in FIG. 1, the combination opening 20 includes a first hole 22 overlapping a second hole 24. One of the holes 22 may be configured to be the locking hole 22, thereby able to receive and secure the locking fastener 30 to the plate 10, and the other of the holes 24 may be configured to be the dynamic compression hole 24, thereby allowing the non-locking fastener 40 to freely move in the hole 24 and apply dynamic compression. The locking hole 22 may have one or more locking features designed to engage with a locking fastener 30, and the dynamic compression hole 24 may be elongated, for example, along the central longitudinal axis A of the plate 10. The screw holes 22, 24 are not constrained to parallel axes. This hole geometry may be used in bone plates 10 to utilize either fixed angle or variable angle locking screws 30 and/or polyaxial non-locking screws 40 that can achieve dynamic compression.

The plate 10 may comprise any suitable number of openings 20 in any suitable configuration. As shown, the plate 10 is a generally an elongate plate 10 including six combination openings 20 positioned along the central longitudinal axis A of the plate 10. The combination openings 20 may also be oriented in any suitable orientation such that the locking holes 22 and dynamic compression holes 24 are optimized based on the type and location of the fracture. As shown, starting from the second end 14 of the plate 10, three of the combination openings 20 are aligned such that the dynamic compression holes 24 are positioned toward the second end 14, and the three combination openings 20 past the midline of the plate 10, are reversed and aligned such that the dynamic compression holes 24 are now positioned toward the first end 12 of the plate.

These openings 20 allow surgeons more flexibility for fastener placement, based on preference, anatomy, and fracture location. Surgeons may have differing opinions as to whether non-locking or locking screws 30, 40 (or some combination of the two) should be used in diaphyseal bone. Further, complexity of fracture location and shape makes having as many locations for fasteners 30, 40 as possible necessary. This design offers surgeons a versatile method to achieve higher accuracy in placement of locking and/or non-locking screws 30, 40.

Figure 4:
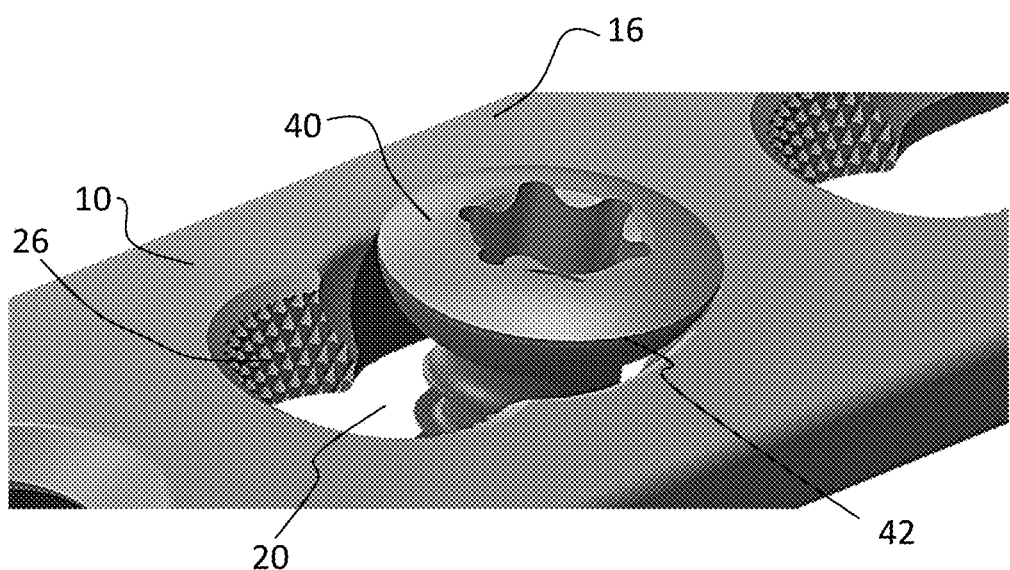
FIG. 4 shows the head of the fastener engaged with a portion of the combination hole.
Figure 5:
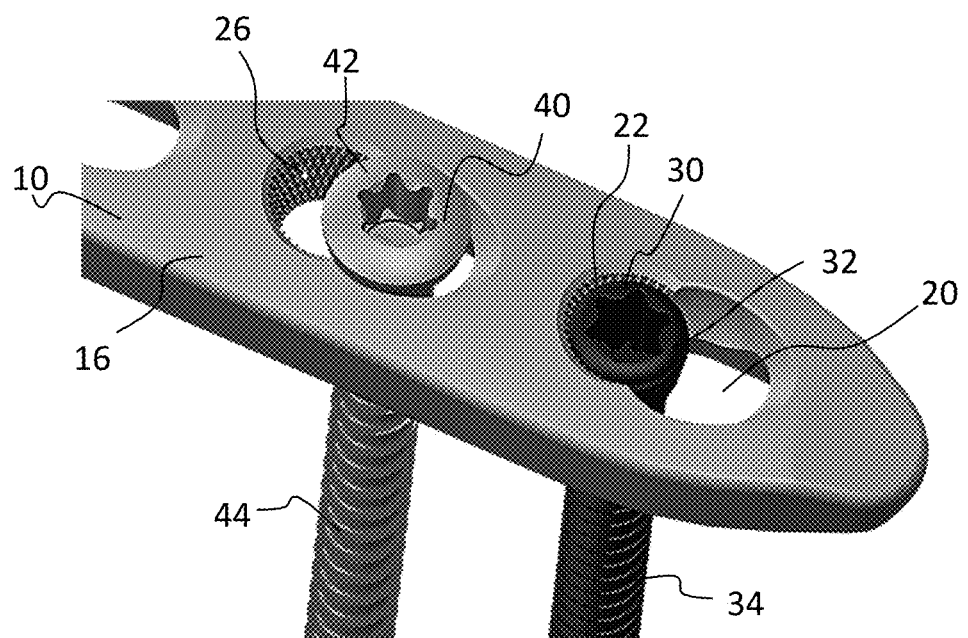
FIG. 5 is a top perspective view of two fasteners engaged with the two combination holes.
Figure 6:
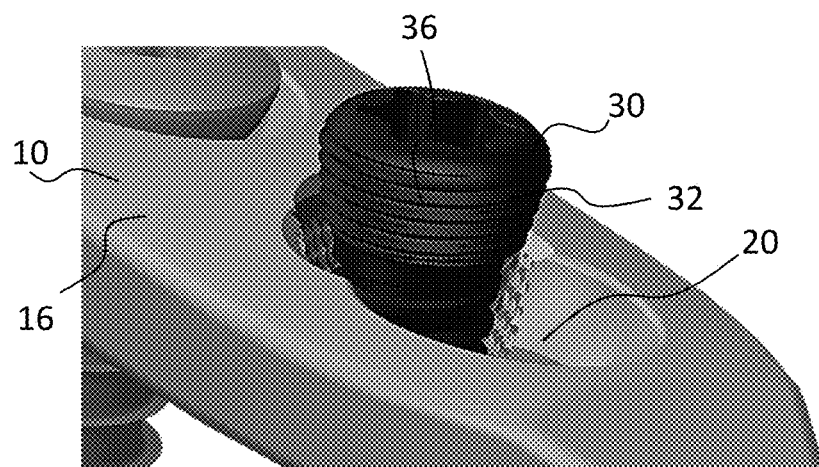
FIG. 6 is a close-up perspective view of the fastener head before engaging the textured portion of the combination hole.

As best seen in FIGS. 4-6, the locking and non-locking fasteners 30, 40 are shown. The locking and non-locking fasteners 30, 40 may include traditional fasteners known in the art. The locking and non-locking fasteners 30, 40 may comprise bone screws or the like. The fasteners 30, 40 may also include other fasteners or anchors configured to be secured or engaged with bone, such as nails, spikes, staples, pegs, barbs, hooks, or the like. The fasteners 30, 40 may include fixed and/or variable angle bone screws.

The locking fastener 30 may include a head portion 32 and a shaft portion 34 configured to engage bone. The shaft portion 34 may be threaded such that the fastener 30 may be threaded into the bone. The head portion 32 of the locking fastener 30 includes a textured area 36 around its outer surface sized and configured to engage with the locking hole 22 of the combination opening 20. The textured area 36 may include threads, ridges, bumps, dimples, serrations, or other types of textured areas. As shown, the texture area 36 preferably includes a threaded portion extending substantially from the top of the head portion 32 to the bottom of the head portion 32 proximate to the shaft portion 34. Thus, when the textured area 36 engages the locking hole 22, the locking fastener 30 is thereby locked to the plate 10.

The non-locking fastener 40 includes a head portion 42 and a shaft portion 44 configured to engage bone. The shaft portion 44 may be threaded such that the fastener 40 may be threaded into the bone. The head portion 42 of the non-locking fastener 40 is substantially smooth around its outer surface such that is able to slide along the elongated compression hole 24. Thus, the non-locking fastener 30 may be coupled to the plate 10, but not locked thereto to enable dynamic compression of the bone. It will be recognized that the head portions 32, 42 of the fasteners 30, 40 may include a recess configured to receive a driver or the like.

As best seen in FIGS. 2 and 4, the locking hole portion 22 of the combination opening 20 includes a textured portion 26. The textured portion 26 may include threads, ridges, bumps, dimples, serrations, knurls, or other types of textured areas. The textured portion 26 may be of the same type (e.g., mating surfaces) or different from the textured area 36 of the locking fastener 30. As shown, the textured portion 26 is serrated or knurled along an inner portion of the hole 22. The knurled surface may include straight, angled, or crossed lines cut or rolled into the material. In the embodiment shown in FIG. 1-6, the textured portion 26 extends along substantially the entire inner surface of the hole 22. With reference to the embodiment shown in FIGS. 7-9, the combination hole 20 is substantially the same as that shown in FIGS. 1-6 except that the textured portion 26 the locking hole 22 now includes a thin centralized textured ribbon of material. For example, the textured portion 26 takes up about half or less of the surface area of the hole 22. In this instance, only a portion of the textured area 36 of the head portion 32 of the locking fastener 30 engages with and locks to the textured portion 26 of the hole 22.

Figure 7:
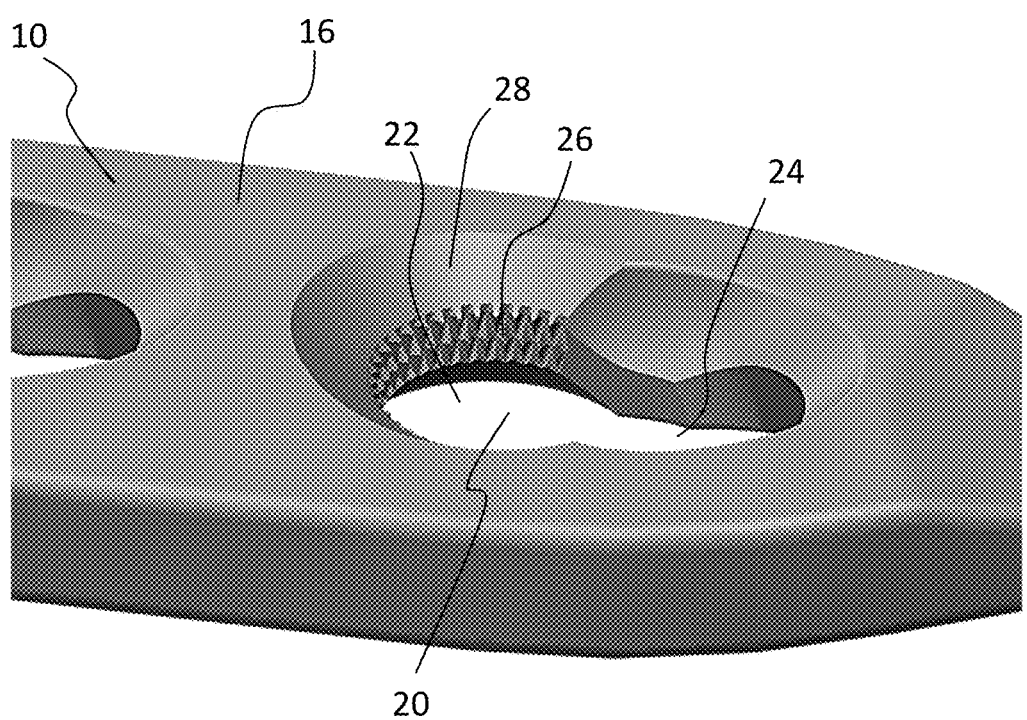
FIG. 7 is a close-up view of an alternative version of a combination hole according to another embodiment.
Figure 8:
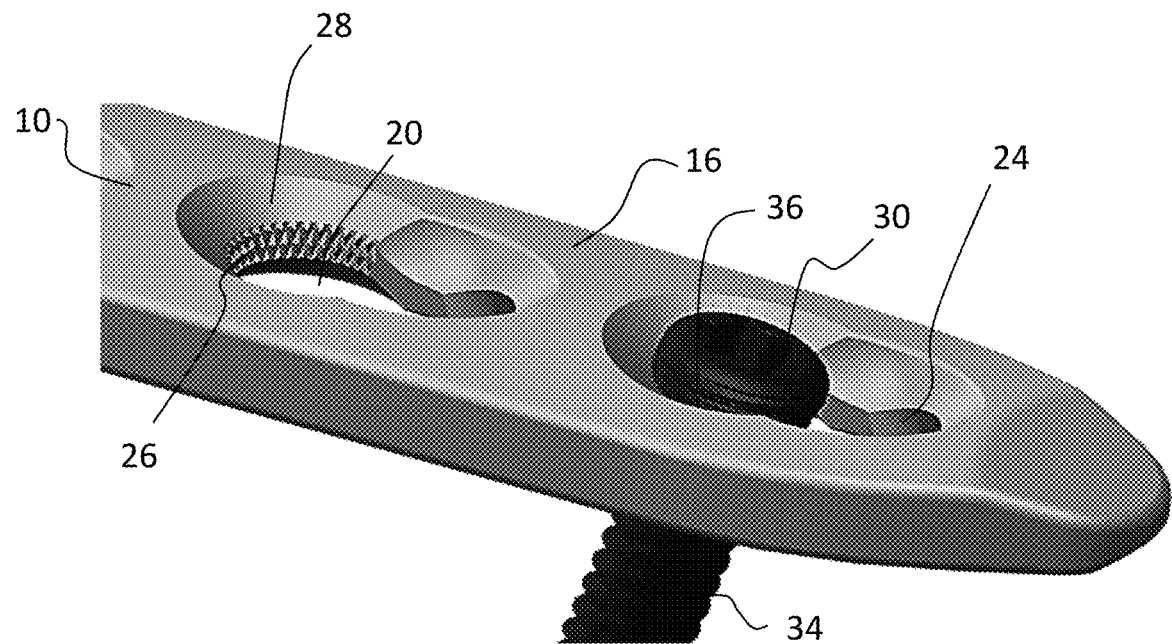
FIG. 8 is a perspective view of a fastener inserted through the combination hole of FIG. 7.
Figure 9:
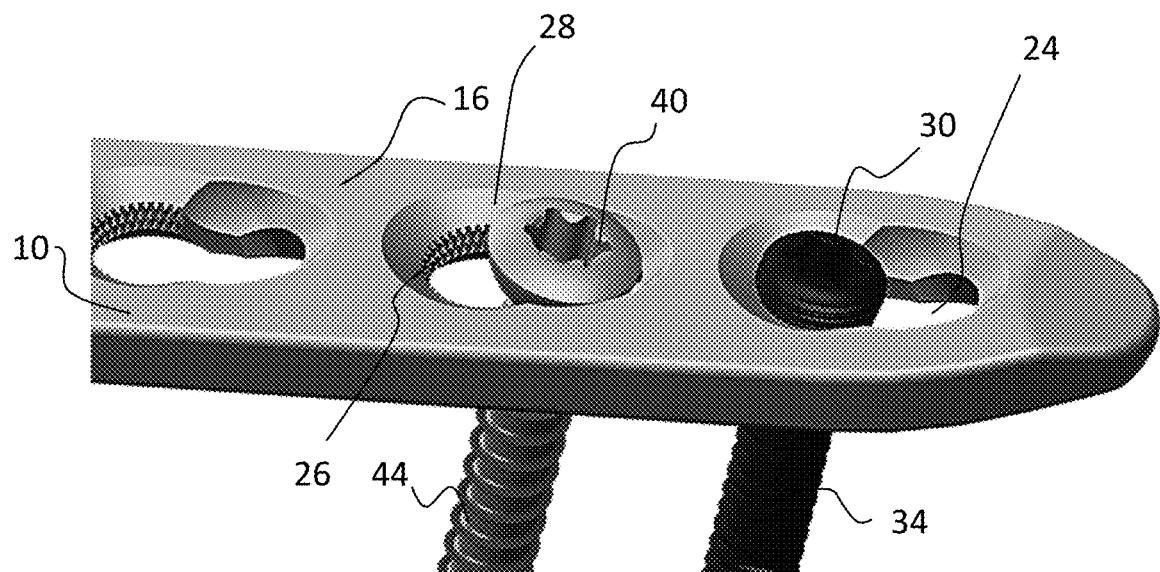
FIG. 9 is a perspective view of two fastener inserted through the combination holes of FIG. 7.

An upper portion of the hole 22 may be tapered 28, without texturing, for example, to facilitate alignment of the fastener 30 with the opening 20. As shown in FIGS. 6-8, this tapered portion 28 is enlarged in area relative to the embodiment in FIGS. 1-5. The hole 22 may be configured to receive a fixed or variable angle fastener 30. The hole 22 may be generally conical in shape such that it is wider near the top surface 16 of the plate 10 and narrower toward the bottom surface 18 of the plate 10. The tapered portion 28 and/or the textured area 26 may be conical in shape. In this embodiment, the locking hole 22 is a textured fixed angle conical hole configured to receive locking fastener 30. The textured holes 22 may deform as the fastener head 32 interferes with the textured portion 26 of the hole 22, thereby providing a positive lock between the fastener 30 and the plate 10.

The second hole portion 24 of the combination opening 20 may be an elongated dynamic compression hole. The dynamic compression hole 24 may be elongated such that it has a length greater than its width. The hole 24 may be elongated along the longitudinal axis A of the plate 10. In the alternative, the hole 24 may be generally cylindrical such that the hole 24 only permits polyaxial movement of the fastener 40. The inner surface of the hole 24 may be substantially smooth such that the non-locking fastener 40 is able to freely pivot and/or slide along the elongated hole 24. This provides for at least two directions of compressive force (e.g., along the longitudinal axis A and perpendicular to the longitudinal axis A). The head portion 42 of the non-locking fastener 40 may be substantially smooth around its outer surface. The head portion 42 is sized and configured to engage with and be retained within the hole portion 24 of the combination opening 20. The hole 24 may be configured to receive a fixed or variable angle fastener 40. In one embodiment, the hole 24 may be generally conical in shape and/or tapered such that it is wider near the top surface 16 of the plate 10 and narrower toward the bottom surface 18 of the plate 10. In this embodiment, the hole 24 is a smooth variable angle conical hole configured to receive the non-locking fastener 40. The hole 24 may receive the fastener head 42 allowing movement of the fastener 40, for example, in a polyaxial fashion and/or along the length of the hole 22, thereby providing dynamic compression of the bone.

The plate 10 may have one or more additional features. For example, the plate 10 may include one or more through holes 50 extending through the plate 10. For example, holes 50 may extend from the top surface 16 to the bottom surface 18 of the plate 10. These holes 50 may be configured to receive k-wires (not shown). In the embodiment shown, six holes 50 are provided along the central longitudinal axis A of the plate 10 to receive one or more k-wires. Although it will be appreciate that any number and location of holes 50 may be provided for receiving k-wires. The plate 10 may also include one or more reliefs to minimize contact of the plate 10 with the bone and preserve the anatomy. For example, the relief may be in the form of one or more conical cuts 52 along the bottom surface 18 of the plate 10. The conical cuts 52 may be positioned on either side of the k-wire holes 50 and extend outward towards the side surfaces of the plate 10. Each conical cut 52 may include a narrowed portion proximate to the k-wire hole 50 (e.g., along the central longitudinal axis A of the plate 10) and a widened portion proximate to the outer side surfaces. Although twelve conical cuts 52 are provided around the six k-wire holes 50, it is envisioned that the conical cuts 52 may be provided at any suitable location and number as would be recognized by one of skill in the art. The plate 10 may further include one or more perimeter reliefs 54 extending around the bottom surface 18 of the plate 10 to reduce unnecessary contact with bone as an anatomy preserving measure. As shown, the perimeter relief 54 is a cutout in the bottom surface 18 of the plate 10 which extends around the outer perimeter of the plate 10. The perimeter relief 54 is interrupted by each of the conical cuts 52. The perimeter relief 54 generally leaves an outer edge surface (e.g., around the sides and first and second ends 12, 14 of the plate 10) except where interrupted by the conical cuts 52 and a central portion of the bottom surface raised relative to the relief 54. The width and depth of the relief 54 may be of any suitable dimension to provide adequate contact between the plate 10 and the bone while minimizing unnecessary contact to preserve the anatomy.

Turning now to FIGS. 10-18, alternative types of openings 20A-20G, which provide for locking and/or non-locking, dynamic compression are provided. Although only the holes are exemplified in these figures, it will be appreciated that the plate 10 may be of any suitable size, shape, and dimension depending on the plating application. As many of the features of these openings are similar to the combination openings 20 described already for FIGS. 1-9, only the different features will be further explained.

Figure 10A:
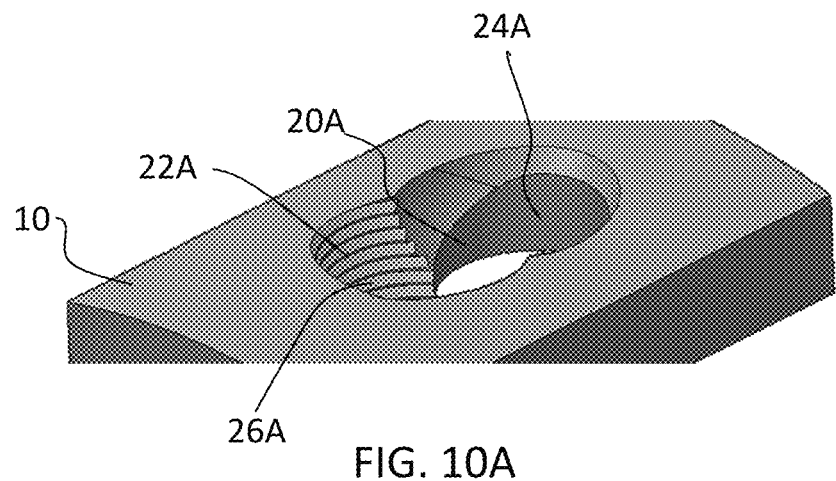
FIGS. 10A-10C show a perspective view, top view, and cross-section view, respectively, of an another embodiment of a combination hole.
Figure 10B:
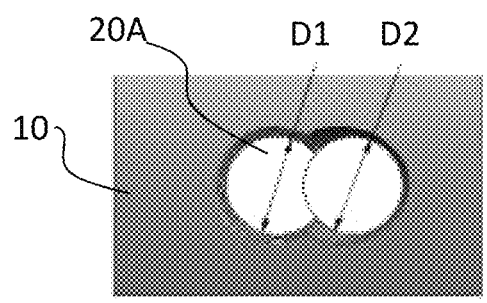
Figure 10C:
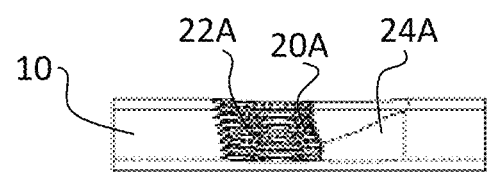

With reference to FIGS. 10A-10C, the combination opening 20A is similar to combination opening 20 except that the dynamic compression hole 24A has the same general diameter as the locking hole 22A, and the locking hole 22A includes a different type of textured portion 26A. In this embodiment, the locking hole 22A has a first diameter D1, and the dynamic compression hole 24A has a second diameter D2. Unlike the elongated hole 24 described earlier, dynamic compression hole 24A has substantially same diameter as the locking hole 22A. Thus, the first and second diameters D1, D2 are substantially the same. The hole 24A may be formed by milling or drilling a sphere out of the plate 10 in the center of the circle with tapers or ramps on either side. The hole 24A is not elongated, but is generally circular and the non-locking fastener 40 will be allowed to translate in the hole 24A because the diameter of the head portion 42 and/or shaft (e.g., bone thread) will be smaller than the size of the hole 24A in the plate 10. With respect to hole 22A, the textured portion 26A of the hole 22A may be in the form of a tapered thread. This tapered thread may generally correspond to a similar tapered thread on the locking fastener 30. This hole 22A also does not include a tapered portion, and the textured portion 26A begins at the intersection with the top surface 16 of the plate 10. This alternative opening 20A also provides for the use of both locking and non-locking fasteners 30, 40 that are able to dynamically compress bone and/or lock the plate 10 to the bone.

Figure 11A:
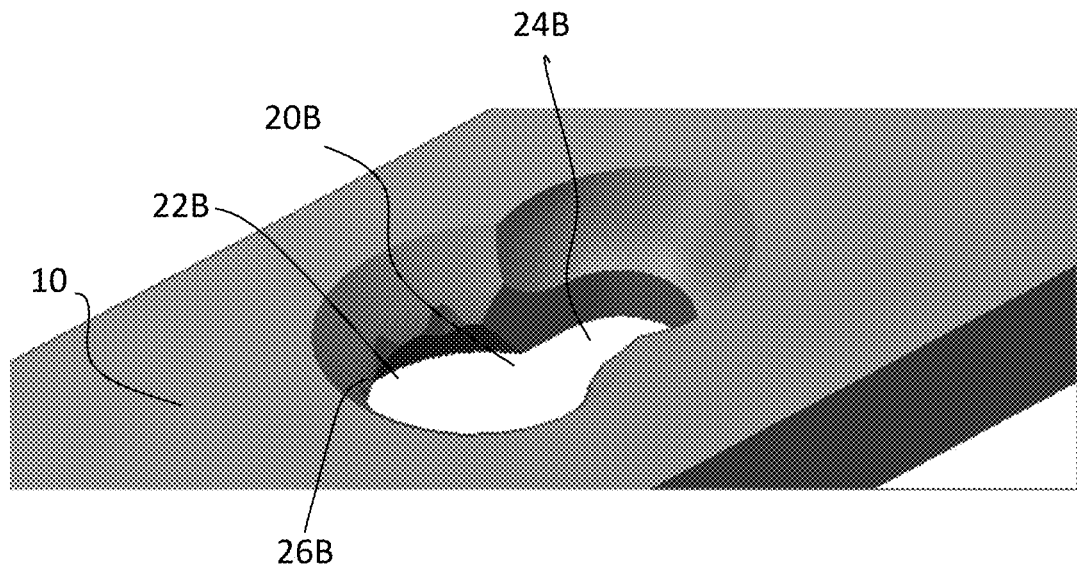
FIGS. 11A-11C show a perspective view, top view, and cross-section view, respectively, of an another embodiment of a combination hole.
Figure 11B:
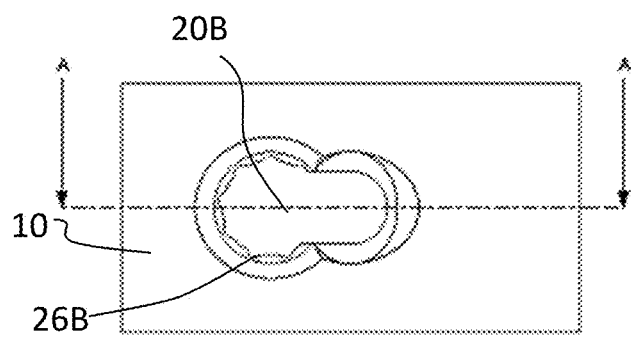
Figure 11C:
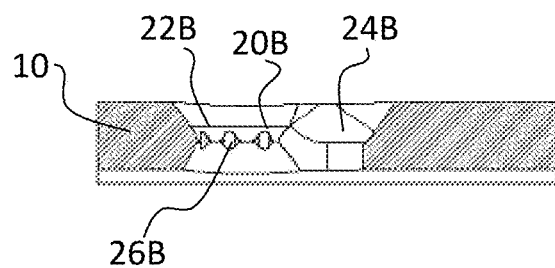

Turning now to FIGS. 11A-11C, the combination opening 20B is similar to other combination openings except that the locking hole 22B includes a different type of textured portion 26B. The textured portion 26B includes a series of alternating recesses and protrusions around a central portion of the hole 22B. The recesses may be in form of a wave of alternating cutouts extending around the inner perimeter of the hole 22B. The textured portion 26B may lock the fastener 30 with a friction fit or may be modified during insertion of the fastener 30 to form a lock in situ. In this embodiment, the locking hole may allow for polyaxial locking. The plate 10 and the locking fastener 30 may be made of dissimilar materials having dissimilar hardness values. For example, the fastener 30 may have a higher hardness (e.g., on the Rockwell scale) relative to the plate 10, which may be formed of a material having a lower relative hardness value. Due to the increased hardness, the head portion 32 of the locking fastener 30 may create a thread in the plate 10 as the fastener 30 is inserted (e.g., threaded) into the hole 22B, thereby locking the fastener 30 to the plate 10.

Figure 12A:
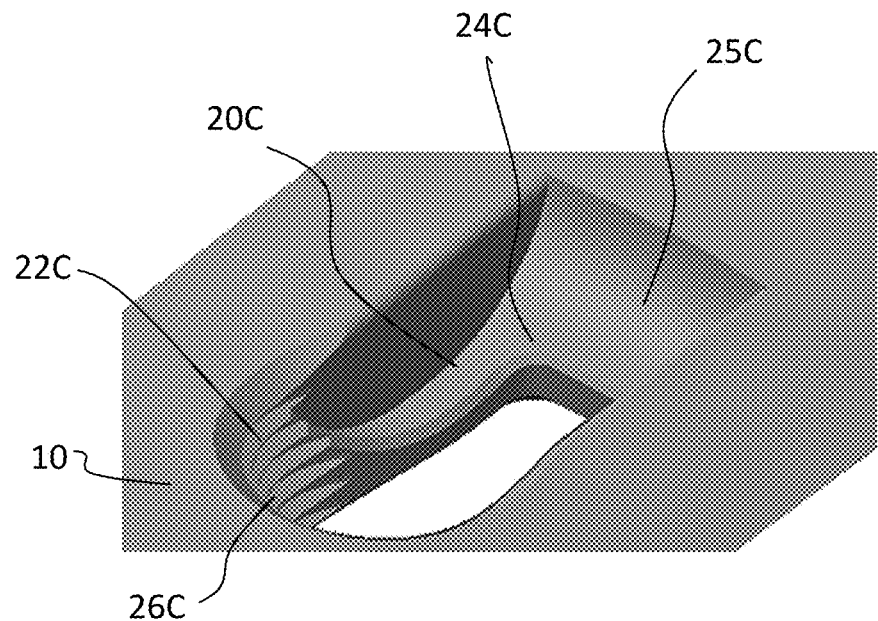
FIGS. 12A-12C show a perspective view, top view, and cross-section view, respectively, of an another embodiment of a hole for receiving a fastener.
Figure 12B:
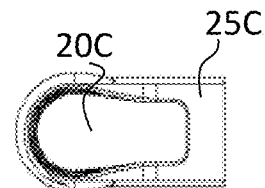
Figure 12C:
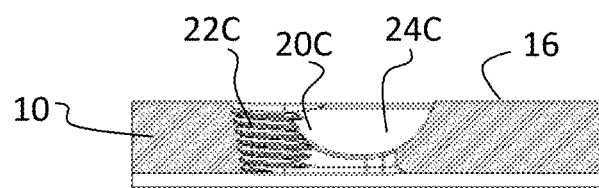

With reference to FIGS. 12A-12C, the opening 20C includes locking hole 22C and dynamic compression hole 24C with a more open configuration. The locking portion 22C has a textured portion 26C in the form of a tapered thread. This tapered thread may generally correspond to a similar tapered thread on the locking fastener 30. The opposite portion 24C of the opening 20C is oblong with a ramp 25C milled into the top surface 16 of the plate 10 to allow for dynamic compression. As best seen in FIG. 12C, the ramp may be partially spherical in shape and extend from the top surface 16 of the plate 10 and connect to the textured portion 26C. When viewed from above in FIG. 12B, the ramp 25C creates a square-like, key-hole, and/or non-hole geometry that sweeps into the tapered threaded locking hole 22C. This alternative opening 20C also provides for the use of both locking and non-locking fasteners 30, 40 that are able to dynamically compress bone and/or lock the plate 10 to the bone.

Figure 13A:
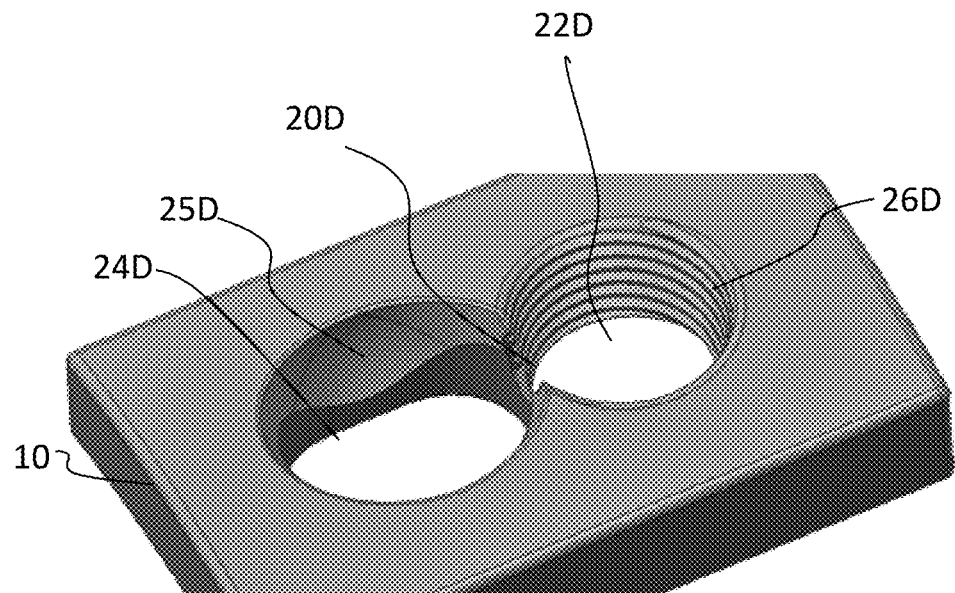
FIGS. 13A-13C show a perspective view, top view, and cross-section view, respectively, of an another embodiment of a combination hole.
Figure 13B:
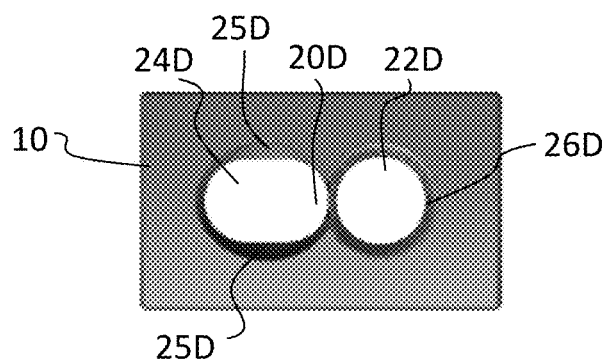
Figure 13C:
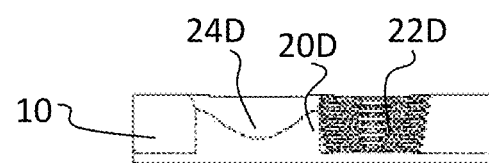

Turning now to FIGS. 13A-13C, the opening 20D includes locking hole 22D and dynamic compression hole 24D. These holes 22D, 24D are connected and close together but are not overlapping. The holes 22D, 24D are separated by a small portion or sliver of plate material proximate to the lower portion of the holes 22D, 24D (e.g., at bottom surface 18 of the plate 10 and partially extending between the holes 22D, 24D). The locking portion 22D has a textured portion 26D in the form of a tapered thread. The textured portion 26D extends around almost the entire circumference of the hole 22D except where connected to hole 24D. The dynamic compression hole 24D is elongated and has ramped portions 25D on opposite sides of the hole 24D to receive fastener 40. This configuration allows for a very close population of holes 22D, 24D on the plate 10 while giving structural stability at the holes 22D, 24D.

Figure 14A:
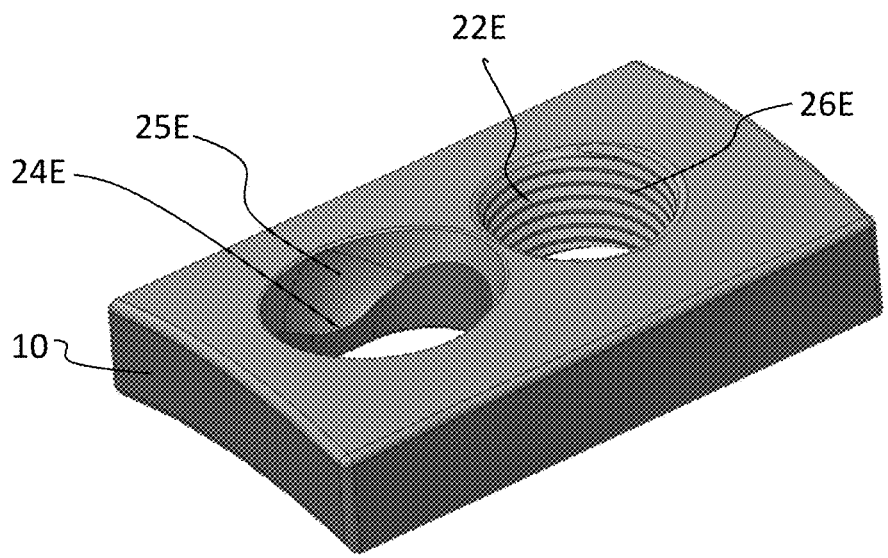
FIGS. 14A-14C show a perspective view, top view, and cross-section view, respectively, of an another embodiment of separate locking and non-locking holes.
Figure 14B:
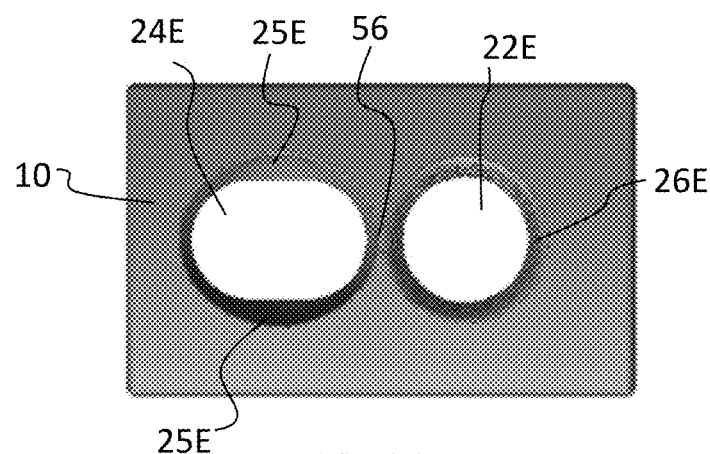
Figure 14C:
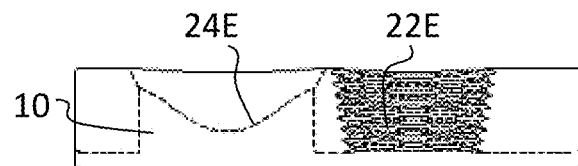

With reference to FIGS. 14A-14C, locking hole 22E and dynamic compression hole 24E are adjacent, but separate from one another. The holes 22E, 24E are completely separated from one another by a wall 56 of plate material. The locking portion 22E has a textured portion 26E in the form of a tapered thread extends around the entire perimeter of the hole 22E. The dynamic compression hole 24E is elongated and has ramped portions 25E on opposite sides of the hole 24E. This configuration also allows for a very close population of holes 22E, 24E on the plate 10 while giving options for both locking and/or dynamic compression.

Figure 15A:
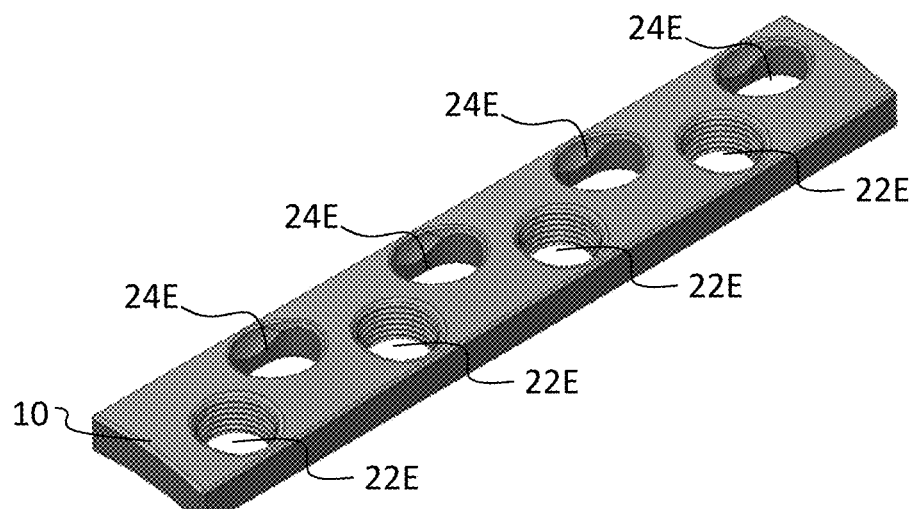
FIGS. 15A-15C show a perspective view, top view, and cross-section view, respectively, of one embodiment of a plate including the separate locking and non-locking holes.
Figure 15B:
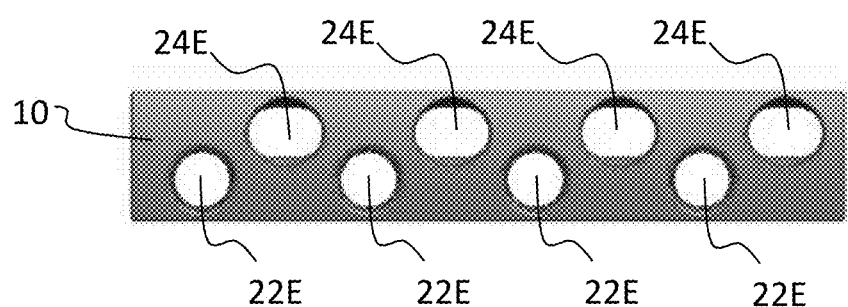
Figure 15C:
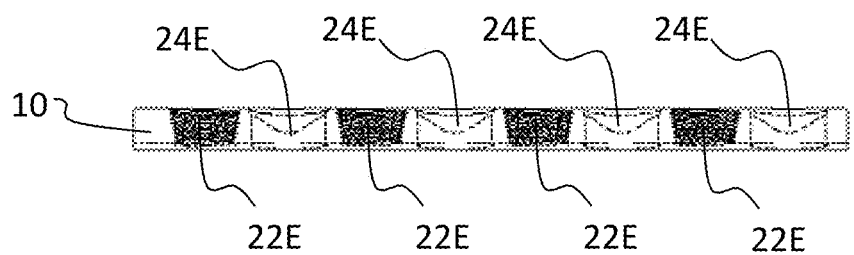
Figure 16A:
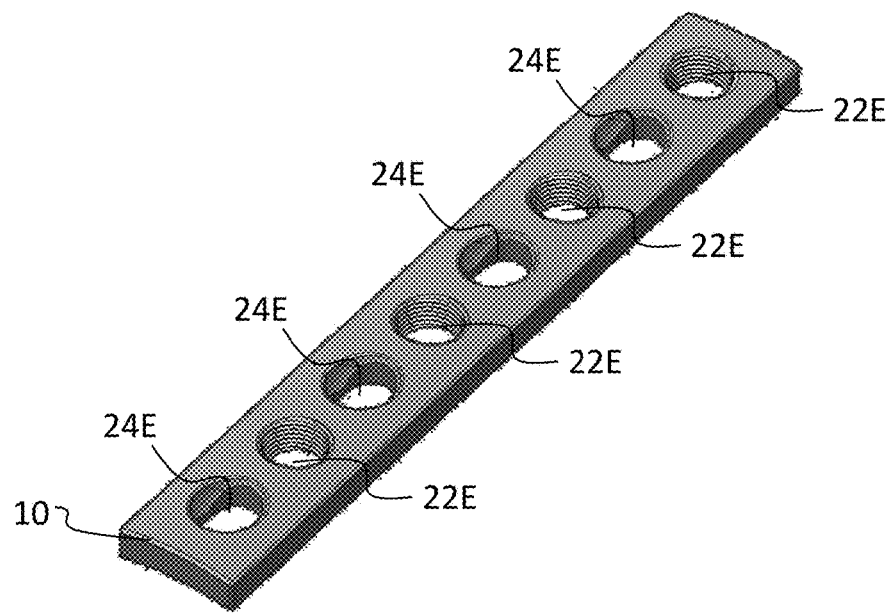
FIGS. 16A-16C show a perspective view, top view, and cross-section view, respectively, of another embodiment of a plate including the separate locking and non-locking holes.
Figure 16B:
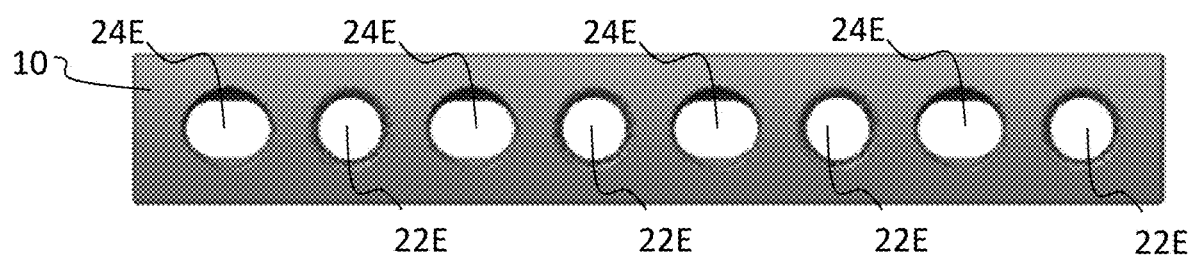
Figure 16C:
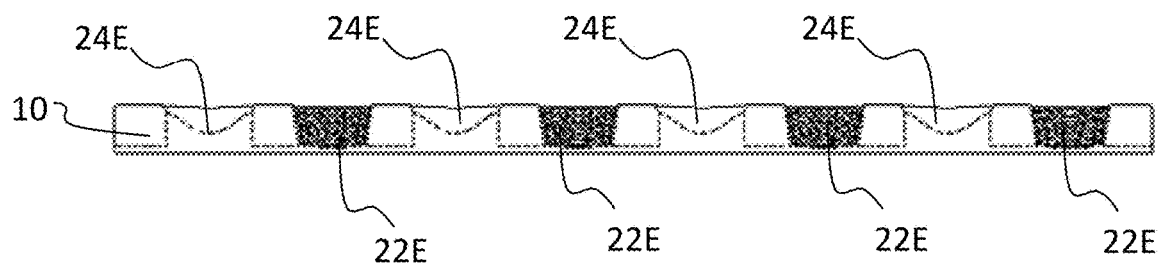

FIGS. 15A-15C and 16A-16C show alternative arrangements of locking holes 22E and dynamic compression holes 24E on plate 10. As shown in FIGS. 15A-15C, the locking and non-locking holes 22E, 24E are staggered over the length of the plate 10. A first series of locking holes 22E are arranged in a first line along the length of the plate 10, and a second series of non-locking holes 24E are arrange in a second line along the length of the plate 10. The first line of holes 22E are offset relative to the second line of holes 24E such that every other hole will be non-locking or locking. Although depicted in straight lines, it is contemplated that the holes 22E, 24E may not necessarily be arranged in a straight line. In FIGS. 16A-16C, the locking and non-locking holes 22E, 24E are staggered along the length of the plate 10 such that each hole alternates between a locking hole 22E and a non-locking hole 24E. The holes 22E, 24E are generally aligned along the central longitudinal axis of the plate 10, but it will be appreciated that the holes may be offset or aligned in any suitable number and configuration along the plate 10.

Turning now to FIGS. 17A-17D, an alternative version of opening 20F is provided. In this embodiment, the hole construct 20F is comprised of at least three overlapping conical threaded holes in the plate 10. The opening 20F includes a first, locking hole 22F, a second hole 24F, and a third hole 23F arranged along a longitudinal axis of the plate 10. The third hole 23F is the mirror image of hole 24F across the first locking hole 22F. The conically threaded holes 22F, 23F, 24F may or may not have parallel axes. Each hole 22F, 23F, 24F may include a textured portion 26F, for example, in the form of one or more threaded portions. Thus, the locking fastener 30 may lock to any of the holes 22F, 23F, 24F. Although each of the holes 22F, 23F, 24F are shown in with the textured portion 26F, it will be appreciated that one or more of the holes 22F, 23F, 24F may have a substantially smooth inner portion instead of the textured portion 26F. The upper part of the hole construct at the first and second ends of the hole 20F each have a ramped feature 25F (e.g., adjacent to holes 23F and 24F) to allow for dynamic compression of the plate 10. In addition, the ramped feature 25F may span the three or more conical holes 22F, 23F, 24F (e.g., around the entire perimeter of the opening 20F).

Figure 17A:
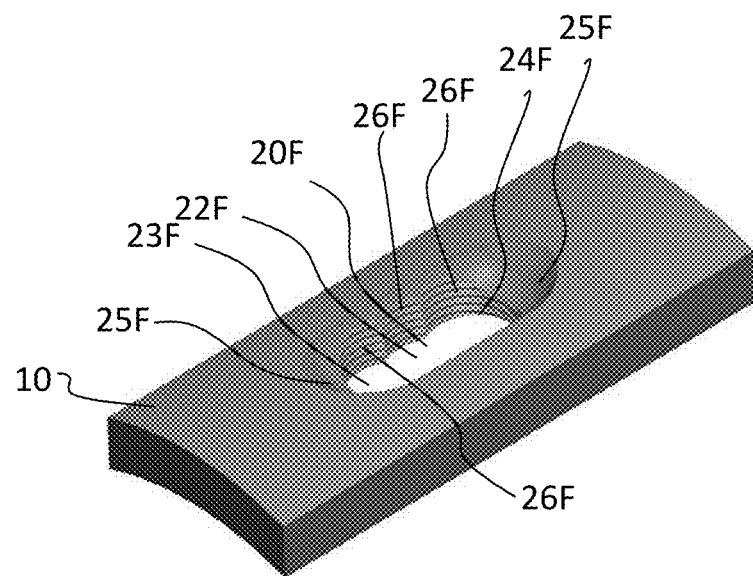
FIGS. 17A-17D show a perspective view, a top view, a cross-section view, and a perspective view with a locking fastener, respectively, according to another embodiment of a plate including three overlapping locking and non-locking holes.
Figure 17B:
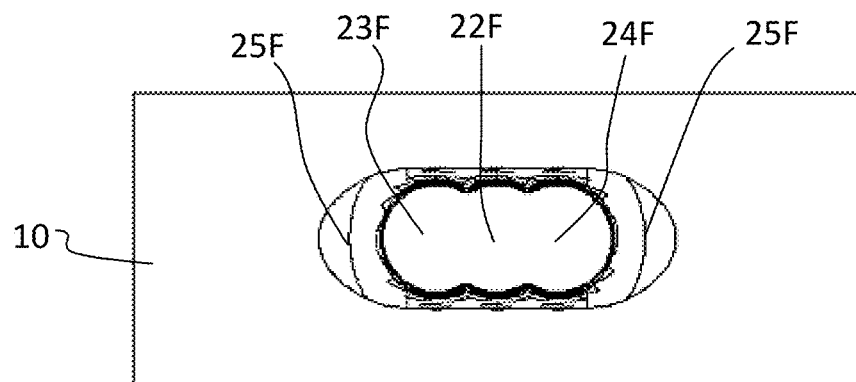
Figure 17C:
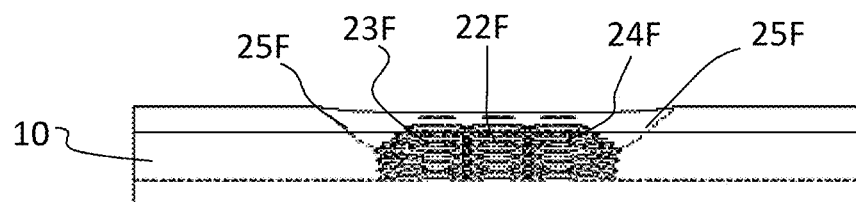
Figure 17D:
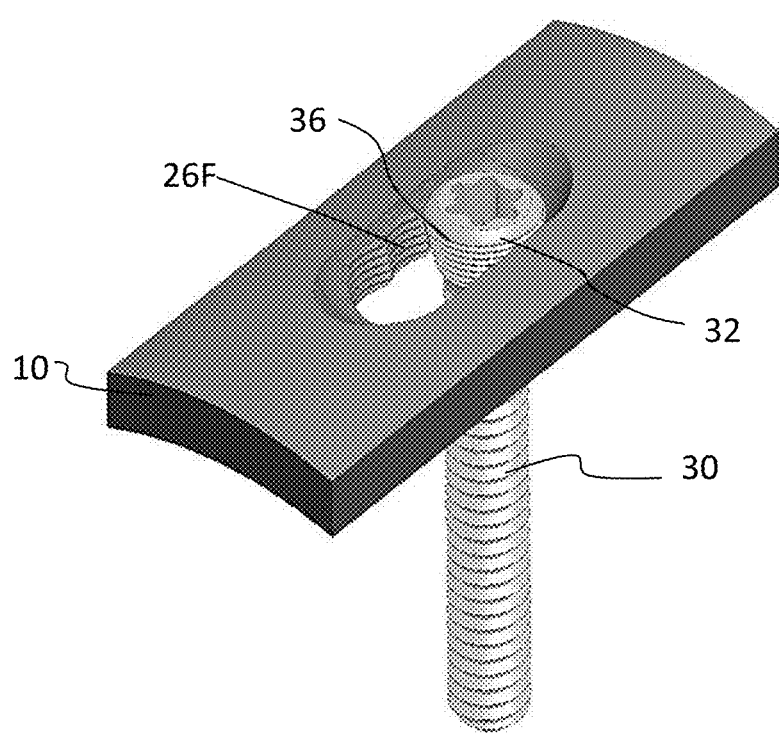

The non-locking compression fasteners 40 may have a major bone thread diameter such that the fastener 40 can translate between overlapping holes 22F, 24F, 23F without interference. As best seen in FIG. 17D, the locking fastener 30 may include a textured area 36, for example, in the form of a thread, configured to engage with the textured portion 26F of any of the holes 22F, 23F, 24F. The hole geometry of opening 20F can be applied to bone plates 10 to utilize either fixed angle and/or variable angle locking screws 30 and/or polyaxial non-locking screws 40 that can achieve dynamic compression. This allows surgeons more flexibility for screw placement, based on preference, anatomy, and fracture location.

Figure 18A:
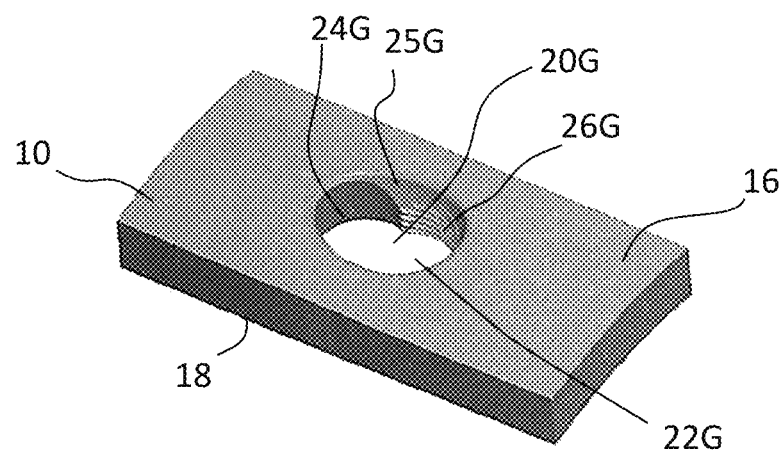
FIGS. 18A-18B show perspective views of a plate according to another embodiment with locking and non-locking functionality.
Figure 18B:
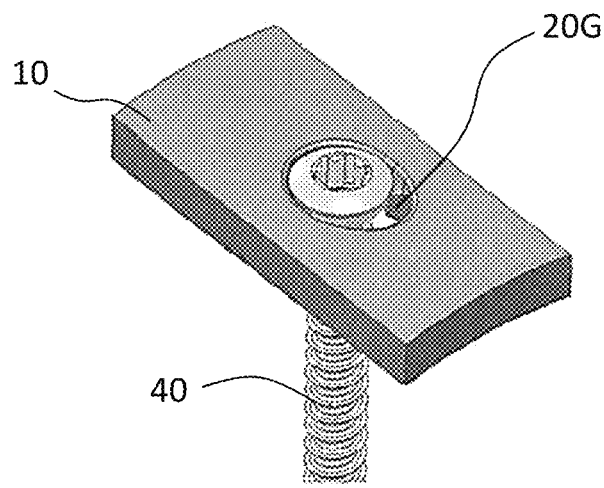

Turning now to FIGS. 18A-18B, another embodiment of opening 20G is provided. This opening 20G may be comprised of one elongate hole or slot extending from the top surface 16 to the bottom surface 18 of the plate 10. A locking portion 22G of the opening 20G may include a textured portion 26G having straight machine threads. The threads may extend more than 180 degrees to retain the locking fastener 30. A non-locking portion 24G of the opening 20G may be positioned opposite the locking portion 22G to complete the opening 20G. The upper part of the opening 20G may have one or more ramped features 25G to allow for dynamic compression of the plate 10. The ramp 25G may span along the entire upper perimeter of the elongated slot 20G or a portion thereof. The compression screws 40 may have a major bone thread diameter such that the screws 40 are able to translate along the opening 20G without interference.

Figure 19A:
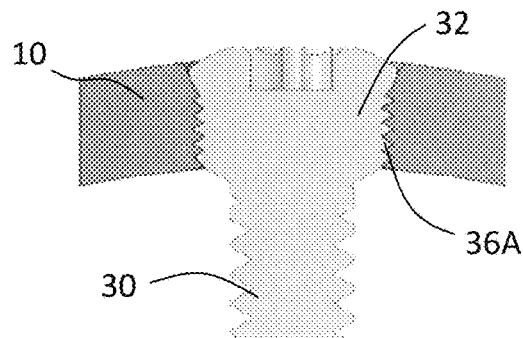
FIGS. 19A-19E shows alternative locking screw and openings in plates according to yet another embodiment.
Figure 19B:
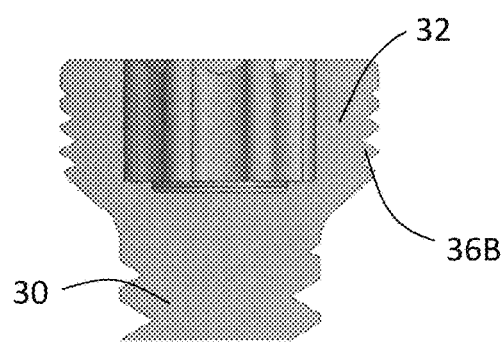
Figure 19C:
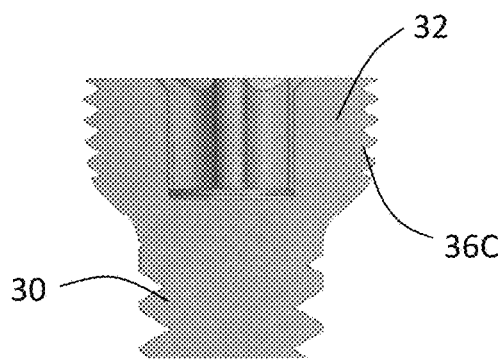
Figure 19D:
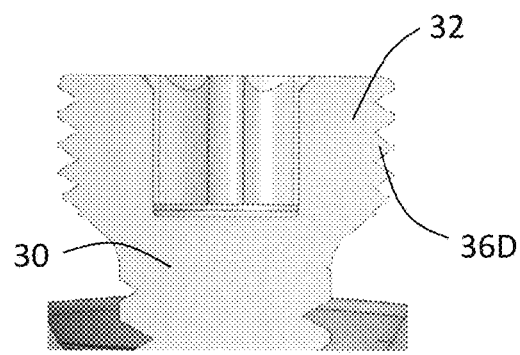
Figure 19E:
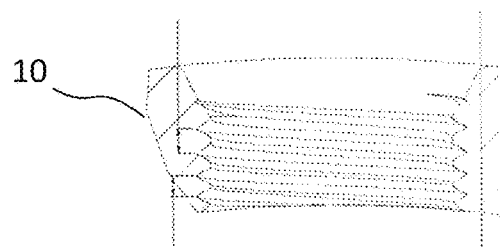

With reference to FIGS. 19A-19E, alternative embodiments of the locking fastener 30 may be used with any plate 10. The head portion 32 of the fastener 30 may include a textured area 36 in the form of a thread, for example, to lock the fastener 30 to the plate 10. The fastener 30 and/or plate 10 may also include one or more mechanisms to prevent back out of the fastener 30 from the plate 10. In FIG. 19A, the head portion 32 includes at threaded portion 36A (e.g., having straight threads) that interface with the plate 10 and the top of the head extends larger than the threads. The head portion 32 bottoms out when the fastener 30 is fully inserted and creates preload in the fastener 30, thus locking the fastener 30 rotationally. In FIG. 19B, the head portion 32 includes threaded portion 36B. The head portion 32 has a constant major diameter while the minor diameter is tapered. The thread depth may go to zero at the top of the head portion 32 of the screw 30. The first few turns smoothly insert, but as the tapered portion of the male thread engages with the plate 10, interference occurs, jamming and/or locking the screw 30 and preventing backout. In FIG. 19C, a screw thread 36C on the head portion 32, similar to the design in FIG. 19B, except the minor diameter of the screw 30 stays constant while the major diameter of the head portion 32 gets larger toward the top of the screw 30. A similar jamming and locking mechanism results through tightening of the screw 30 in the plate 10. In FIG. 19D, the threaded portion 36D has areas of varying pitch. In particular, a straight screw thread on the head portion 32 of the screw 30 has a similar pitch to that of the plate 10 at the bottom of the head portion 32 of the screw 30. The pitch then increases or decreases towards the top of the head portion 32, which thereby results in jamming of the threads and preventing unwanted backout of the screw 30. In an alternative variation of the concept of FIG. 19D, shown in FIG. 19E, the opening in the plate 10 is provided with areas of varying pitch while the pitch of the threaded portion 36D remains constant. For example, the head portion 32 may include a straight thread with a constant pitch. The upper surface of the plate 10 may include a thread pitch is similar to that of the screw 10, but towards the bottom surface of the plate 10, the thread pitch would either increase or decrease to lock the screw 30 to the plate 10.

Figure 20A:
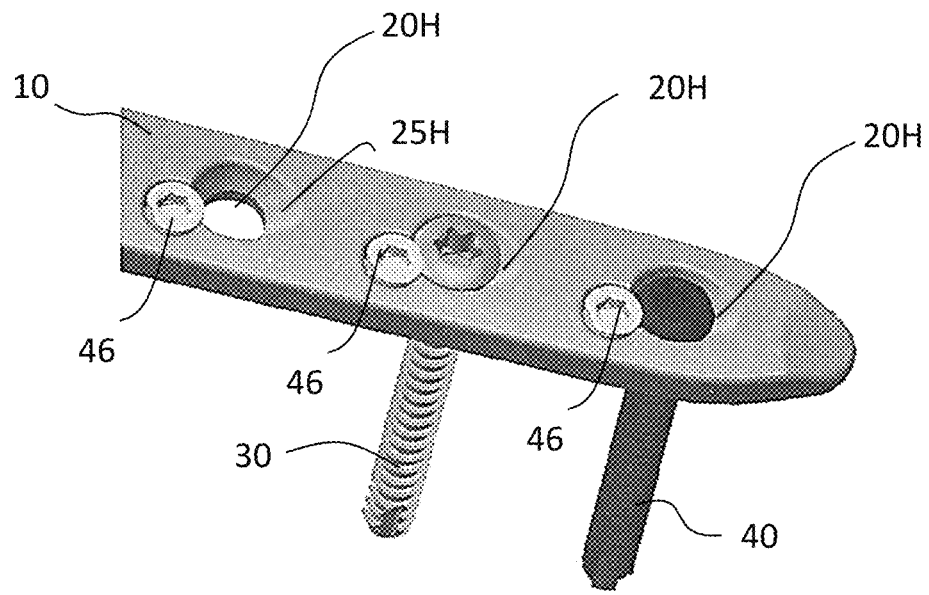
FIGS. 20A and 20B depict a perspective view and cross-section view of an alternative version of a plate with blocking screws.
Figure 20B:
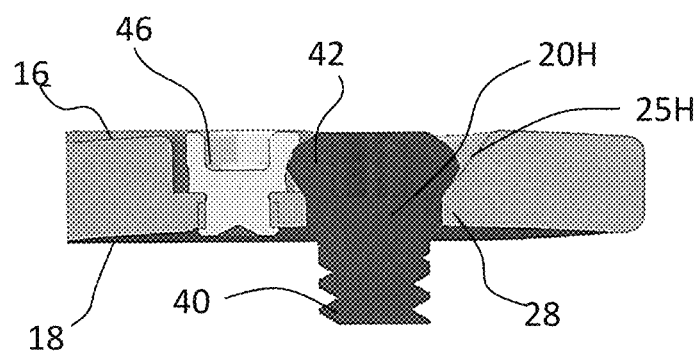

Turning now to FIGS. 20A and 20B, the plate 10 includes an additional anti-backout feature. In this embodiment, the plate 10 includes cylindrical holes or openings 20H configured to accept either the compression fastener 40 or the locking fastener 30. Each opening 20H may include a ramped portion 25H extending around a portion or the entire perimeter of the opening 20H to allow for dynamic compression with a compression fastener 40. Each opening 20H may include a cylindrical feature to provide angular stability with a locking fastener 30. The opening 20H may also include an angular taper 28 to cause compressive tightening between the locking fastener 30 and the cylindrical opening 20H. Each opening 20H has an accompanying blocking screw 46 that can be actuated to block the fastener 30, 40 from backing out. The blocking screw 46 may extend from a first end at the top surface 16 to a second end at the bottom surface 18 of the plate 10. The first end of the blocking screw 46 may include a recess sized to receive an instrument to rotate the blocking screw 46 from an unblocked position to a blocked position. The blocked position may include a portion of the blocking screw 46 covering a portion of the head portion 42 of the fastener 40, thereby further preventing backout of the fastener 40 from the plate 10.

According to yet another embodiment, the plate 10 may include one or more openings 20 configured to receive the locking fastener 30 having self-forming threads that work by displacement of the plate material to lock the fastener 30 to the plate 10. Turning now to FIGS. 21-26, the locking fastener 30 and alternative embodiments of the openings 20 in the plate 10 are shown. In these embodiments, the locking mechanism of the fastener 30 (e.g., bone screw) to the internal fixation plate 10 may allow for variable angle screw insertion. The fastener 30 may be inserted within an angular cone where the force required to dislodge the head portion 32 of the fastener 30 is substantially equivalent to the force required when the fastener 30 is inserted perpendicular to the plate 10. The holes or openings 20 in the plate 10 may be shaped such that the fastener 30 may be inserted at different angles. The geometry of the opening 20 is conducive to catching the threads on the head portion 32 of the fastener 30 and to reduce the axial force necessary to initiate the thread formation.

The locking mechanism includes a fastener 30 having a head portion 32 with self-forming threads that displace the plate material. The plate 10 may be made of a material softer than the fastener 30 to facilitate displacement. For example, the plate 10 may be comprised of titanium, alloys, polymers, or other materials having a lower material hardness (e.g., Rockwell hardness). The fastener 30 may be made of a harder relative material, for example, comprised of cobalt chrome, tungsten, alloys, or other materials having a higher material hardness. Preferably, the fastener 30 is comprised of a material having a strong, stiff, and high surface hardness which facilitates the thread forming process. The forming mechanism works by displacement of material rather than removal of the material of the plate 10, thereby minimizing fragments or chips which are created from tapping.

Figure 21A:
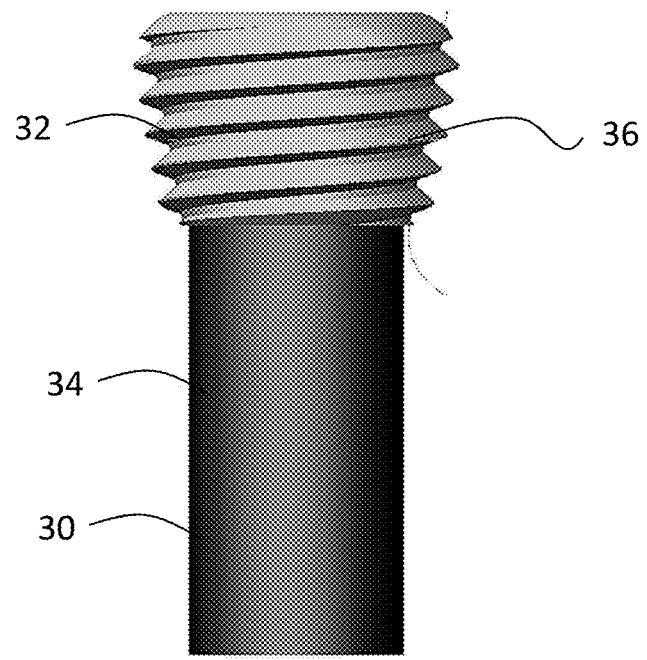
FIGS. 21A and 21B depict a fastener according to another embodiment with self-forming threads configured to form threads in the opening of a plate.
Figure 21B:
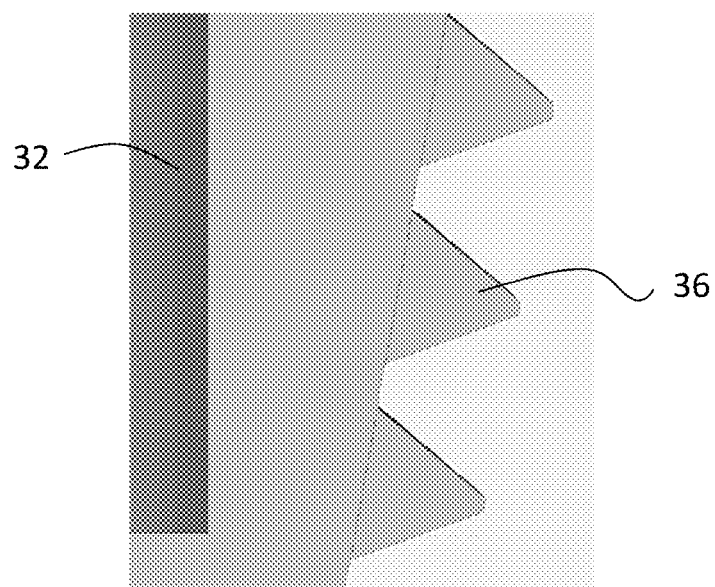
Figure 22A:
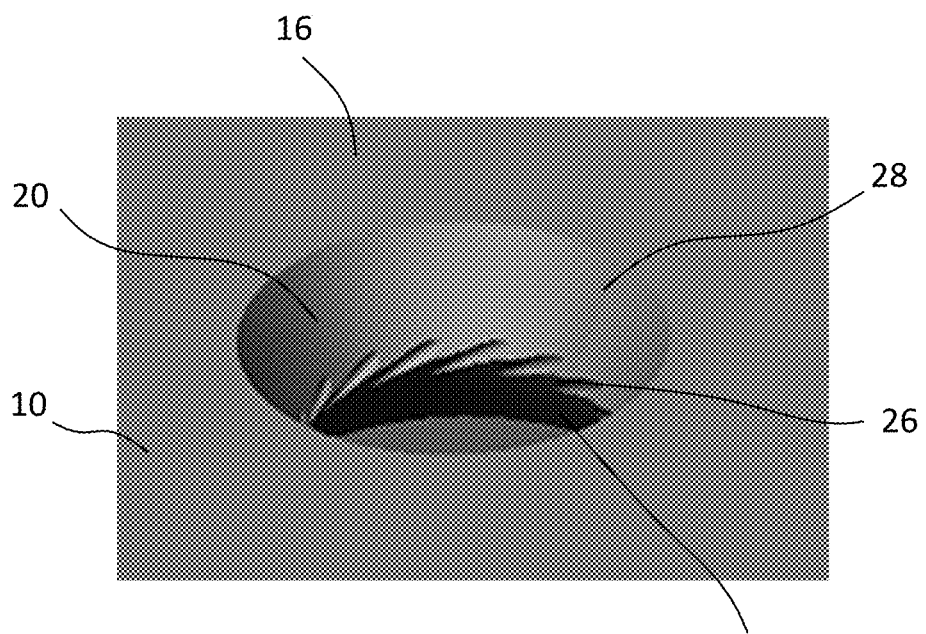
FIGS. 22A and 22B depict an opening in a plate according to one embodiment having a windswept cut configured to receive the self-forming threads of the fastener of FIGS. 21A-21B.
Figure 22B:
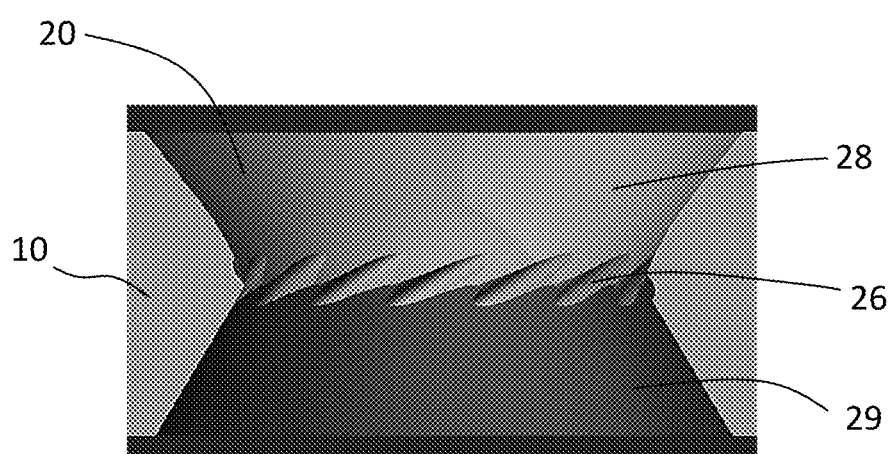

In FIGS. 21A-21B, the locking fastener 30 includes a head portion 32 and a shaft portion 34 configured to engage bone. Although not shown, the shaft portion 34 may be threaded such that the fastener 30 may be threaded into the bone. The head portion 32 may be tapered (e.g., at an angle of about 20°) such that the fit within the opening 20 in the plate 10 becomes tighter as the fastener 30 is advanced in to the bone. The head portion 32 of the locking fastener 30 includes a textured area 36 around its outer surface sized and configured to engage an opening 20 in the plate 10. The textured area 36 may include threads, ridges, bumps, dimples, serrations, or other types of textured areas. As shown, the textured area 36 preferably includes a threaded portion extending substantially from the top of the head portion 32 to the bottom of the head portion 32 proximate to the shaft portion 34. The threads 36 may run generally perpendicular to the conical surface of the head portion 32. The threaded portion 36 is in the form of self-forming threads configured to displace the plate material and create threads in the opening 20 of the plate 10. The threaded portion has an exaggerated sharp thread peak to facilitate cutting or forming of the plate material.

Turning now to FIGS. 22A-25B, alternative versions of the openings 20 are shown before being tapped with the fastener 30. Once the fastener 30 is inserted, these openings 20 are modified based on the self-forming threads. The geometry of the openings 20 are conducive to catching the threads 36 and designed to reduce the axial force necessary to initiate the thread formation. An upper portion of the hole 20 may be tapered 28, for example, with a conical straight tapered surface cut through the top surface 16 of the plate 10 for clearance of the head portion 32 of the fastener 30 during off angle insertion. A lower portion of hole 20 may further be tapered 29, for example, with a conical straight tapered surface cut through the bottom surface 18 of the plate 10 for clearance of the shaft portion 34 during off angle insertion. The upper tapered portion 28 may be larger, for example, with a larger degree of taper than the lower tapered portion 29. For example, the upper tapered portion 28 may have a taper in a range from about 60-90°, 70-80°, or 72-78°, preferably about 70°, 75°, or 80° whereas the lower tapered portion 29 may have a taper in a range from about 50-70°, 55-65°, or 57-63°, preferably about 55°, 60°, or 65°. The upper and/or lowered tapered portions 28, 29 may be substantially conical (e.g., FIGS. 22B, 23B, 24B) or may be segmented with more than one section, such as two separate conical sections having different diameters or degrees of taper (e.g., FIGS. 25A and 25B).

At the intersection between the upper tapered portion 28 and the lower tapered portion 29 a narrowed central portion may have a textured portion 26. As described herein, the textured portion 26 may include threads, ridges, bumps, dimples, serrations, or other types of textured areas. In the embodiment shown in FIGS. 22A-22B, the textured portion 26 includes a windswept cut design comprised of a plurality of shallow cuts where each cut overlaps the next. For example, the windswept design may include a plurality of threadlike helical cut sweeps. Each cut has a smooth transition into the inner diameter of the hole 20 (e.g., into the upper and lower tapered portions 28, 29). The windswept cuts provide a positive surface for the self-forming threads to cut into, thereby helping to prevent peeling of the newly formed threads into the plate 10.

Figure 23A:
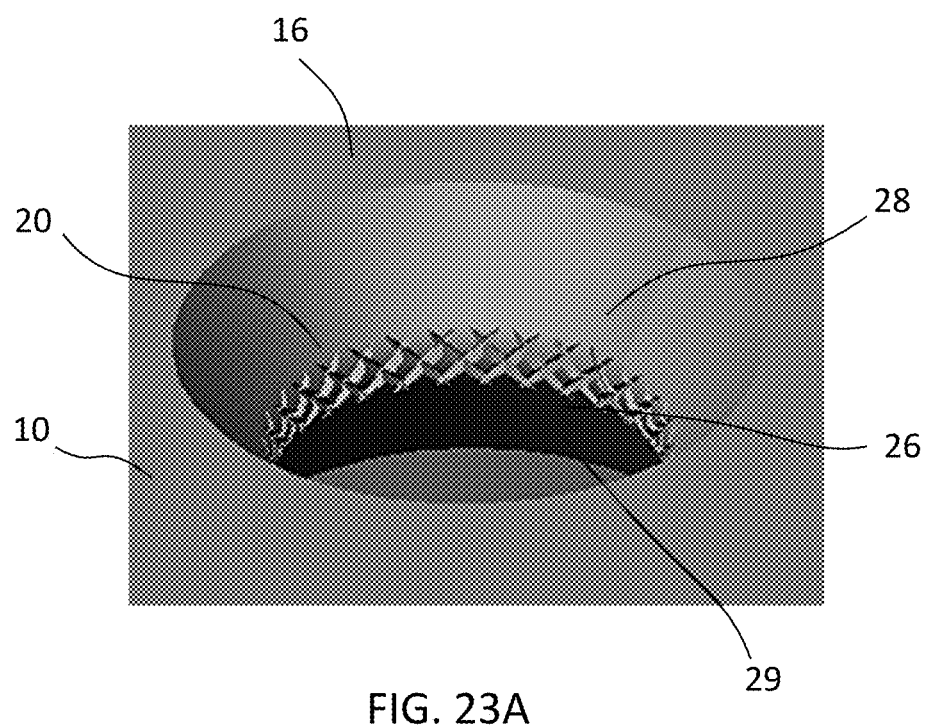
FIGS. 23A and 23B depict an opening in a plate according to another embodiment having a knurled cut configured to receive the self-forming threads of the fastener of FIGS. 21A-21B.
Figure 23B:
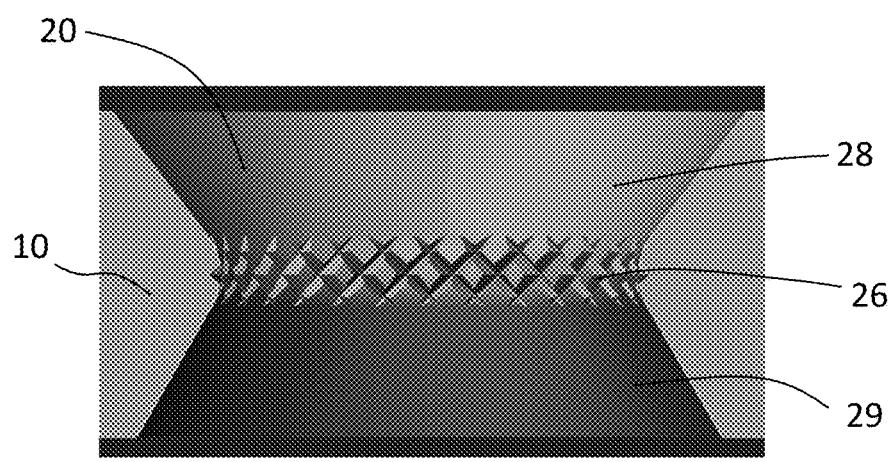
Figure 24A:
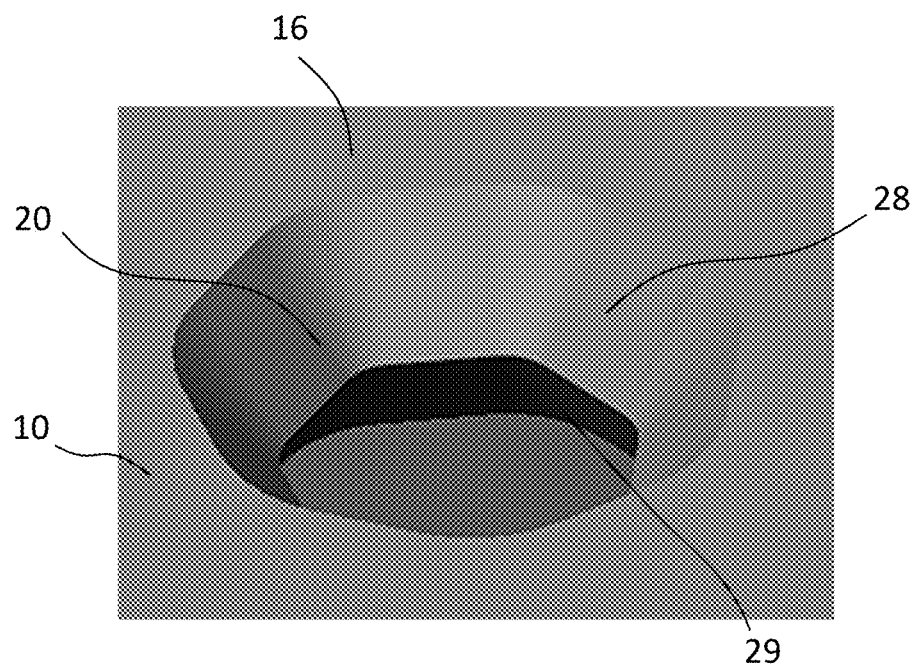
FIGS. 24A and 24B depict an opening in a plate according to another embodiment having a polygonal cut configured to receive the self-forming threads of the fastener of FIGS. 21A-21B.
Figure 24B:
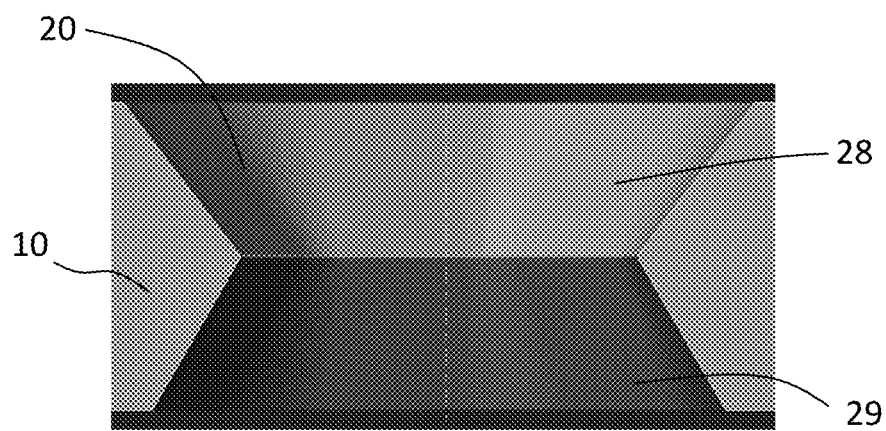

In FIGS. 23A-23B, the textured portion 26 includes a knurled cut design. A rounded transition between the upper tapered portion 28 and the lower tapered portion 29 (e.g., the two conical cuts) provides a workable surface for the knurling process as well as a surface for the head portion 32 to be able to roll over during off-axis locking. The knurled design may include a plurality of shallow knurled grooves set in a diamond pattern (e.g., about 45°) where each cut overlaps the next. The knurled grooves allow for the self-forming threads to cut more deeply into the material and reduce the necessary axial force to begin the thread forming process. FIGS. 24A-24B depict a polygon form cut design. In this design, there is no textured portion at the transition between the upper tapered portion 28 and the lower tapered portion 29. Instead, the narrowed central region has an overall polygonal form such that the hole 20 is neither cylindrical nor conical. The polygonal shape includes a number of sides with distinct linear section of material and rounded corners around which the form cut is allowed to sweep. For example, the polygonal shape may be substantially hexagonal (6-sided), heptagonal (7-sided), octagonal (8-sided), etc. The hole 20 may also be represented without lobe cuts, as a single concentric ring with the same geometry.

Figure 25A:
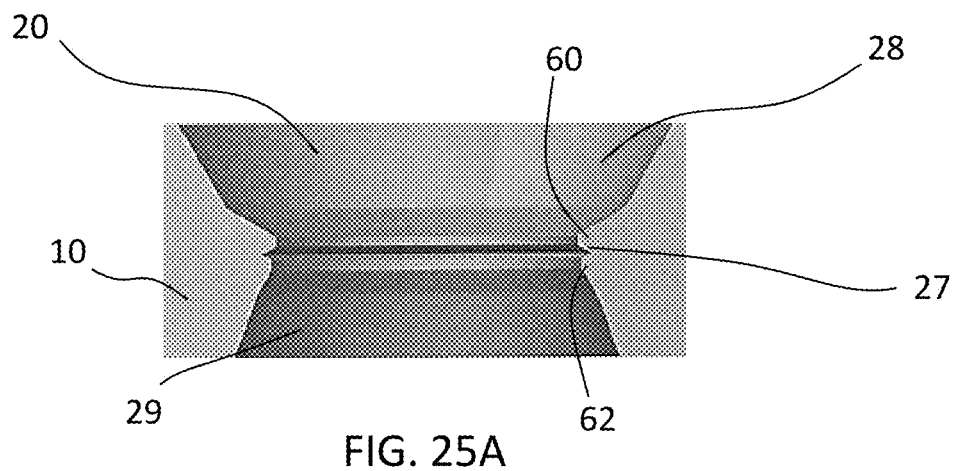
FIG. 25A depicts an alternative opening in a plate according to another embodiment.

In FIG. 25A, the upper tapered portion 28 includes a conical straight tapered surface cut for clearance of the head portion 32 of the fastener 30 during off angle insertion. The upper tapered portion 28 is segmented to have an upper area with a larger area relative to a lower area proximate the transition to the lower tapered portion 29 having a narrower diameter. The central area between the upper and lower tapered portions 28, 29, where the thread forming process occurs, includes two peaks or concentric rings of material (e.g., a superficial ring 60 and a deep ring 62) with a groove 27 being locating in between for material removal and thread forming relief. The groove 27 between the rings 60, 62 may be angled, for example, in the range of about 40-80°, about 50-70°, or about 60°. The superficial ring 60 is of a slightly smaller inner diameter than the deep ring 62, as the superficial ring 60 is responsible for supporting a majority of the cantilever loads. The deep ring 62 provides additional fixation and support during off-angle insertion as well as additional support during nominal trajectory insertion. The lower tapered portion 29 includes a straight tapered surface that provides clearance for the shaft 34 of the fastener 30 when inserted off angle.

Figure 25B:
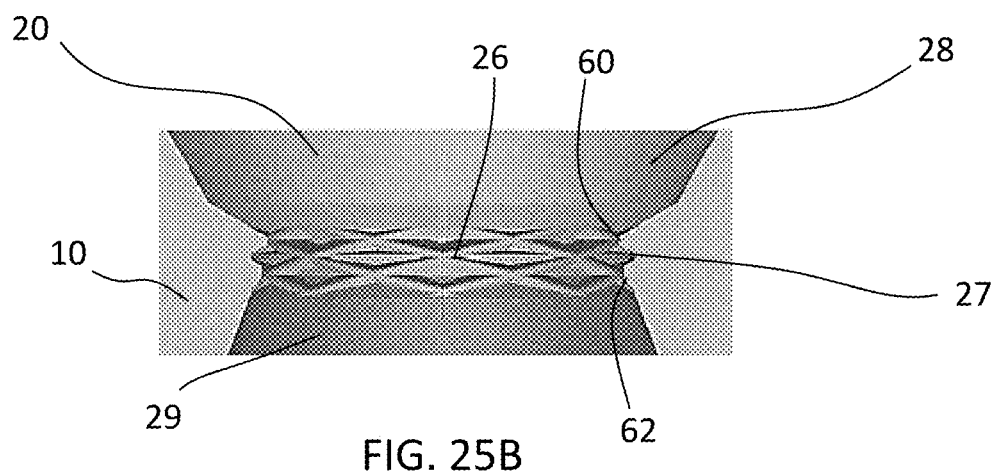
FIG. 25B depicts another alternative opening in a plate according to yet another embodiment.

The embodiment of the opening 20 in FIG. 25B is similar to FIG. 25A, but further includes textured portion 26 in the form of a plurality of helical swept cuts at the transition between the upper tapered portion 28 and the lower tapered portion 29. The shallow helical cuts or windswept cuts may include a series of cuts at a steep pitch. The windswept cuts may be angled, for example, at about 50-70°, or about 60°. The same number of cuts may be made in both a clockwise and counter-clockwise fashion. The cuts may create plateaus of material protruding into the opening 20. The resultant geometry provides positive surfaces for the fastener 30 to cut into, which can dramatically reduce the axial force necessary to lock the fastener 30 to the plate 10. Thus mechanism does not need to rely on bone purchase in order to engage the threads in the head portion 32 of the fastener 30. The material removed during insertion of the fastener 30 allows the self-forming threads to cut deeper by removing material which much be formed and reducing friction between the fastener 30 and the plate 10 during the forming process.

FIGS. 26A-26D depict a screw-plate assembly. The assembly, in FIG. 26C, shows the locking fastener 30 placed at an angle, other than perpendicular, to the upper surface 16 of the plate 10. In FIG. 26D, a non-locking fastener 40 is placed generally perpendicular to the plate 10. It will be appreciated that the locking fastener 30 and non-locking fastener 40 may be oriented at any appropriate angle relative to the plate 10. The section view in FIG. 26C shows the thread engagement with the plate 10 in which material of the plate 10 is displaced around the threads of the fastener 30. By using the self-forming threads, the fastener 30 is able to be inserted into the plate 10 at variable angles and engages with the plate 10 with one-step locking requiring no additional steps to lock the fastener 30 to the plate 10. The section view in FIG. 26D show the compressive, non-locking screw 40 received in the opening 20, without threadedly locking thereto. The non-locking screw 40 may provide for dynamic compression of the bone. Accordingly, the fasteners and openings described herein provide a wide variety of options for the surgeon, thereby providing appropriate locking and/or unlocking capability for dynamic compression depending on the desired treatment of the fracture and the bone.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A stabilization system comprising:
   a bone plate having an upper surface and a lower surface configured to be in contact with bone, the bone plate having an opening extending from the upper surface to the lower surface, the opening including a combination of a compression hole formed by a first bore having a first bore axis and a locking hole formed by a second bore having a second bore axis different from the first bore axis, the locking hole including a textured portion and the compression hole including a non-textured portion, wherein the textured portion comprises a texture that is a non-threaded surface, wherein the textured portion comprises a knurled surface including a pattern of non-perpendicular crossed lines cut into the plate; and
   a fastener configured to be received by the opening and configured to be inserted into the bone, wherein the fastener is either a locking fastener or a compression fastener, the locking fastener having a threaded head portion configured to engage the textured portion and lock to the bone plate.

2. The stabilization system of claim 1, wherein the opening is generally conical in shape such that it is wider near the upper surface of the plate and narrower toward the lower surface of the plate.

3. The stabilization system of claim 1, wherein at least one of the first and second bores includes an elongated opening.

4. The stabilization system of claim 1, wherein the textured portion further comprises a pattern of straight or angled lines cut into the plate.

5. The stabilization system of claim 1, wherein the opening includes an upper conical straight tapered surface extending from the upper surface of the plate, a lower conical straight tapered surface extending from the lower surface of the plate, and an intersection between the upper tapered surface and the lower tapered surface forming a narrowed central portion comprising the textured portion.

6. The stabilization system of claim 5, wherein the upper tapered surface has a larger degree of taper than the lower tapered surface.

7. The stabilization system of claim 6, wherein the upper tapered surface has a taper in a range from about 70-80° and the lower tapered surface has taper in a range from about 55-65°.

8. The stabilization system of claim 1, further comprising a blocking screw configured to cover a portion of the fastener in a locked position to prevent the fastener from backing out of the plate.

9. The stabilization system of claim 1, wherein the threaded head portion is a self-forming thread configured to displace material of the plate to lock the fastener to the plate.

10. A stabilization system comprising:
a bone plate having an upper surface and a lower surface configured to be in contact with bone, the bone plate having an opening a plurality of openings extending from the upper surface to the lower surface, at least one opening including a combination of a compression hole formed by a first bore having a first bore axis and a locking hole formed by a second bore having a second bore axis different from the first bore axis, the locking hole including a textured portion and the compression hole including a non-textured portion, wherein the textured portion comprises a texture that is a non-threaded surface, wherein the textured portion comprises a knurled surface including a pattern of non-perpendicular crossed lines cut into the plate;
a locking fastener configured to be received by one of the openings and configured to be inserted into the bone, wherein the locking fastener has a threaded head portion configured to lock to the bone plate; and
a compression fastener configured to be received by one of the openings and configured to be inserted into the bone, wherein each opening is configured to receive either the locking fastener or the compression fastener.

11. The stabilization system of claim 10, wherein the opening is generally conical in shape such that it is wider near the upper surface of the plate and narrower toward the lower surface of the plate.

12. The stabilization system of claim 10, wherein at least one of the first and second bores includes an elongated opening.

13. The stabilization system of claim 10, wherein the textured portion further comprises a pattern of straight or angled lines cut into the plate.

14. The stabilization system of claim 10, further comprising a blocking screw configured to cover a portion of the fastener in a locked position to prevent the fastener from backing out of the plate.

15. The stabilization system of claim 10, wherein the threaded head portion is a self-forming thread configured to displace material of the plate to lock the fastener to the plate.

16. A stabilization system comprising:
a bone plate having an upper surface and a lower surface configured to be in contact with bone, the bone plate having an opening extending from the upper surface to the lower surface, the opening including a combination of a compression hole formed by a first bore having a first bore axis and a locking hole formed by a second bore having a second bore axis different from the first bore axis, the locking hole including a textured portion and the compression hole including a non-textured portion, wherein the textured portion comprises a texture that is a non-threaded surface, wherein the textured portion comprises a knurled surface including a pattern of non-perpendicular crossed lines cut into the plate;
a locking fastener configured to be received by the opening and configured to be inserted into the bone, wherein the locking fastener has a threaded head portion configured to lock to the bone plate; and
a compression fastener configured to be received by the opening and configured to be inserted into the bone.

\* \* \* \* \*